(12) United States Patent
Lichtenstein

(10) Patent No.: US 9,918,706 B2
(45) Date of Patent: Mar. 20, 2018

(54) CLOSING OPENINGS IN ANATOMICAL TISSUE

(71) Applicant: Kardium Inc., Burnaby (CA)

(72) Inventor: Samuel Lichtenstein, Vancouver (CA)

(73) Assignee: KARDIUM INC., Burnaby (CA)

( * ) Notice: Subject to any disclaimer, the term of this patent is extended or adjusted under 35 U.S.C. 154(b) by 287 days.

(21) Appl. No.: 14/694,521

(22) Filed: Apr. 23, 2015

(65) Prior Publication Data
US 2015/0223791 A1 Aug. 13, 2015

Related U.S. Application Data

(62) Division of application No. 13/112,695, filed on May 20, 2011, now Pat. No. 9,050,066.
(Continued)

(51) Int. Cl.
| | | |
|---|---|---|
| *A61B 17/00* | (2006.01) | |
| *A61B 17/08* | (2006.01) | |
| *A61B 17/10* | (2006.01) | |
| *A61B 17/068* | (2006.01) | |
| *A61B 17/22* | (2006.01) | |
| *A61B 17/29* | (2006.01) | |
| *A61B 90/00* | (2016.01) | |

(Continued)

(52) U.S. Cl.
CPC .... *A61B 17/0057* (2013.01); *A61B 17/00234* (2013.01); *A61B 17/068* (2013.01);
(Continued)

(58) Field of Classification Search
CPC .............. A61B 17/0057; A61B 17/068; A61B 2017/00477; A61B 2017/00557;
(Continued)

(56) References Cited

U.S. PATENT DOCUMENTS

| | | |
|---|---|---|
| 3,132,438 A | 5/1964 | Ward et al. |
| 4,114,202 A | 9/1978 | Roy et al. |

(Continued)

FOREIGN PATENT DOCUMENTS

| | | |
|---|---|---|
| WO | 90/15582 A1 | 12/1990 |
| WO | 01/78625 A1 | 10/2001 |

(Continued)

OTHER PUBLICATIONS

Mack, Michael J., "New Techniques for Percutaneous Repair of the Mitral Valve", Heart Failure Review, 2006; 11:259-268.
(Continued)

*Primary Examiner* — Julian W Woo
(74) *Attorney, Agent, or Firm* — Rossi, Kimms & McDowell LLP

(57) ABSTRACT

A device for closing at least one opening leading to an anatomical cavity is delivered via a catheter positioned in a first opening leading to the anatomical cavity. An orientation control unit is positioned within the anatomical cavity. The orientation control unit defines an orientation of a portion of a tissue surface within the anatomical cavity that is skewed with respect to the first opening and orients a closure member of the device with the tissue surface. An occluding member and a constricting unit of the device are positioned within the anatomical cavity with the occluding member blocking a portion of an opening that is constricted by the constricting unit. An intermediate member of the device is positioned within the anatomical cavity and a closure unit employing at least one piercing element pierces through the intermediate member into a tissue wall surrounding the anatomical cavity.

19 Claims, 12 Drawing Sheets

Related U.S. Application Data

(60) Provisional application No. 61/352,277, filed on Jun. 7, 2010.

(52) U.S. Cl.
CPC .............. *A61B 17/08* (2013.01); *A61B 17/10* (2013.01); *A61B 2017/0061* (2013.01); *A61B 2017/00477* (2013.01); *A61B 2017/00557* (2013.01); *A61B 2017/00579* (2013.01); *A61B 2017/00592* (2013.01); *A61B 2017/00623* (2013.01); *A61B 2017/00668* (2013.01); *A61B 2017/22068* (2013.01); *A61B 2017/2927* (2013.01); *A61B 2090/08021* (2016.02)

(58) Field of Classification Search
CPC ........... A61B 2017/00579; A61B 2017/00592; A61B 2017/0061; A61B 2017/00623; A61B 2017/00668; A61B 2017/22068; A61B 2017/2927; A61B 2019/481
See application file for complete search history.

(56) References Cited

U.S. PATENT DOCUMENTS

| | | | |
|---|---|---|---|
| 4,164,046 A | 8/1979 | Cooley | |
| 4,240,441 A | 12/1980 | Khalil | |
| 4,261,342 A | 4/1981 | Aranguren Duo | |
| 4,263,680 A | 4/1981 | Reul et al. | |
| 4,490,859 A | 1/1985 | Black et al. | |
| 4,543,090 A | 9/1985 | McCoy | |
| 4,794,912 A | 1/1989 | Lia | |
| 4,850,957 A | 7/1989 | Summers | |
| 4,890,602 A | 1/1990 | Hake | |
| 4,890,612 A | 1/1990 | Kensey | |
| 4,893,613 A | 1/1990 | Hake | |
| 4,921,499 A | 5/1990 | Hoffman et al. | |
| 5,021,059 A | 6/1991 | Kensey et al. | |
| 5,047,047 A | 9/1991 | Yoon | |
| 5,100,418 A | 3/1992 | Yoon et al. | |
| 5,104,399 A | 4/1992 | Lazarus | |
| 5,122,137 A | 6/1992 | Lennox | |
| 5,156,609 A | 10/1992 | Nakao et al. | |
| 5,192,314 A | 3/1993 | Daskalakis | |
| 5,242,456 A | 9/1993 | Nash et al. | |
| 5,258,000 A | 11/1993 | Gianturco | |
| 5,312,435 A | 5/1994 | Nash et al. | |
| 5,320,632 A | 6/1994 | Heidmueller | |
| 5,364,408 A | 11/1994 | Gordon | |
| 5,366,443 A | 11/1994 | Eggers et al. | |
| 5,366,459 A | 11/1994 | Yoon | |
| 5,368,601 A | 11/1994 | Sauer et al. | |
| 5,374,275 A | 12/1994 | Bradley et al. | |
| 5,423,859 A | 6/1995 | Koyfman et al. | |
| 5,450,860 A | 9/1995 | O'Connor | |
| 5,454,834 A | 10/1995 | Boebel et al. | |
| 5,478,353 A | 12/1995 | Yoon | |
| 5,507,811 A | 4/1996 | Koike et al. | |
| 5,531,760 A | 7/1996 | Alwafaie | |
| 5,593,424 A | 1/1997 | Northrup, III | |
| 5,645,566 A | 7/1997 | Brenneman et al. | |
| 5,702,421 A * | 12/1997 | Schneidt ............ | A61B 17/0057 600/32 |
| 5,713,896 A | 2/1998 | Nardella | |
| 5,716,397 A | 2/1998 | Myers | |
| 5,720,726 A | 2/1998 | Marcadis et al. | |
| 5,728,114 A | 3/1998 | Evans et al. | |
| 5,752,965 A | 5/1998 | Francis et al. | |
| 5,782,861 A | 7/1998 | Cragg et al. | |
| 5,800,495 A | 9/1998 | Machek et al. | |
| 5,824,066 A | 10/1998 | Gross | |
| 5,836,990 A | 11/1998 | Li | |
| 5,861,005 A * | 1/1999 | Kontos .............. | A61B 17/0057 227/175.1 |
| 5,865,791 A | 2/1999 | Whayne et al. | |
| 5,919,207 A | 7/1999 | Taheri | |
| 5,961,440 A | 10/1999 | Schweich, Jr. et al. | |
| 5,964,782 A | 10/1999 | Lafontaine et al. | |
| 5,971,994 A | 10/1999 | Fritzsch | |
| 5,984,950 A | 11/1999 | Cragg et al. | |
| 6,001,069 A | 12/1999 | Tachibana et al. | |
| 6,024,096 A | 2/2000 | Buckberg | |
| 6,074,417 A | 6/2000 | Peredo | |
| 6,074,418 A | 6/2000 | Buchanan et al. | |
| 6,104,944 A | 8/2000 | Martinelli | |
| 6,113,610 A | 9/2000 | Poncet | |
| 6,132,438 A | 10/2000 | Fleischman et al. | |
| 6,203,554 B1 | 3/2001 | Roberts | |
| 6,210,432 B1 | 4/2001 | Solem et al. | |
| 6,221,103 B1 | 4/2001 | Melvin | |
| 6,221,104 B1 | 4/2001 | Buckberg et al. | |
| 6,241,747 B1 | 6/2001 | Ruff | |
| 6,248,124 B1 | 6/2001 | Pedros et al. | |
| 6,258,258 B1 | 7/2001 | Sartori et al. | |
| 6,287,321 B1 | 9/2001 | Jang | |
| 6,304,769 B1 | 10/2001 | Arenson et al. | |
| 6,306,135 B1 | 10/2001 | Ellman et al. | |
| 6,332,864 B1 | 12/2001 | Schweich, Jr. et al. | |
| 6,346,105 B1 | 2/2002 | Tu et al. | |
| 6,348,064 B1 * | 2/2002 | Kanner .............. | A61B 17/0057 411/457 |
| 6,358,258 B1 | 3/2002 | Arcia et al. | |
| 6,358,277 B1 | 3/2002 | Duran | |
| 6,360,749 B1 | 3/2002 | Jayaraman | |
| 6,379,366 B1 | 4/2002 | Fleischman et al. | |
| 6,391,048 B1 | 5/2002 | Ginn et al. | |
| 6,391,054 B2 | 5/2002 | Carpentier et al. | |
| 6,402,680 B2 | 6/2002 | Mortier et al. | |
| 6,402,781 B1 | 6/2002 | Langberg et al. | |
| 6,406,420 B1 | 6/2002 | McCarthy et al. | |
| 6,409,760 B1 | 6/2002 | Melvin | |
| 6,416,459 B1 | 7/2002 | Haindl | |
| 6,436,052 B1 | 8/2002 | Nikolic et al. | |
| 6,450,171 B1 | 9/2002 | Buckberg et al. | |
| 6,475,223 B1 | 11/2002 | Werp et al. | |
| 6,485,489 B2 | 11/2002 | Teirstein et al. | |
| 6,506,210 B1 | 1/2003 | Kanner | |
| 6,537,198 B1 | 3/2003 | Vidlund et al. | |
| 6,537,314 B2 | 3/2003 | Langberg et al. | |
| 6,540,670 B1 | 4/2003 | Hirata et al. | |
| 6,551,312 B2 | 4/2003 | Zhang et al. | |
| 6,569,160 B1 | 5/2003 | Goldin et al. | |
| 6,569,198 B1 | 5/2003 | Wilson et al. | |
| 6,575,971 B2 | 6/2003 | Hauck et al. | |
| 6,589,208 B2 | 7/2003 | Ewers et al. | |
| 6,626,930 B1 | 9/2003 | Allen et al. | |
| 6,629,988 B2 * | 10/2003 | Weadock ............ | A61B 17/11 606/153 |
| 6,632,238 B2 | 10/2003 | Ginn et al. | |
| 6,662,034 B2 | 12/2003 | Segner et al. | |
| 6,676,685 B2 | 1/2004 | Pedros et al. | |
| 6,723,038 B1 | 4/2004 | Schroeder et al. | |
| 6,726,704 B1 | 4/2004 | Loshakove et al. | |
| 6,726,716 B2 | 4/2004 | Marquez | |
| 6,743,241 B2 | 6/2004 | Kerr | |
| 6,749,622 B2 | 6/2004 | McGuckin, Jr. et al. | |
| 6,760,616 B2 | 7/2004 | Hoey et al. | |
| 6,780,197 B2 | 8/2004 | Roe et al. | |
| 6,797,001 B2 | 9/2004 | Mathis et al. | |
| 6,800,090 B2 | 10/2004 | Alferness et al. | |
| 6,824,562 B2 | 11/2004 | Mathis et al. | |
| 6,840,957 B2 | 1/2005 | DiMatteo et al. | |
| 6,852,076 B2 | 2/2005 | Nikolic et al. | |
| 6,855,143 B2 | 2/2005 | Davison et al. | |
| 6,890,353 B2 | 5/2005 | Cohn et al. | |
| 6,899,674 B2 | 5/2005 | Viebach et al. | |
| 6,908,478 B2 | 6/2005 | Alferness et al. | |
| 6,949,122 B2 | 9/2005 | Adams et al. | |
| 6,960,229 B2 | 11/2005 | Mathis et al. | |
| 6,986,775 B2 | 1/2006 | Morales et al. | |
| 6,989,028 B2 | 1/2006 | Lashinski et al. | |
| 6,991,649 B2 | 1/2006 | Sievers | |
| 6,994,093 B2 | 2/2006 | Murphy et al. | |
| 6,997,951 B2 | 2/2006 | Solem et al. | |
| 7,025,776 B1 | 4/2006 | Houser et al. | |

(56) References Cited

U.S. PATENT DOCUMENTS

| | | |
|---|---|---|
| 7,050,848 B2 | 5/2006 | Hoey et al. |
| 7,052,487 B2 | 5/2006 | Cohn et al. |
| 7,101,395 B2 | 9/2006 | Tremulis et al. |
| 7,144,363 B2 | 12/2006 | Pai et al. |
| 7,160,322 B2 | 1/2007 | Gabbay |
| 7,166,127 B2 | 1/2007 | Spence et al. |
| 7,177,677 B2 | 2/2007 | Kaula et al. |
| 7,186,210 B2 | 3/2007 | Feld et al. |
| 7,189,202 B2 | 3/2007 | Lau et al. |
| 7,279,007 B2 | 10/2007 | Nikolic et al. |
| 7,300,435 B2 | 11/2007 | Wham et al. |
| 7,303,526 B2 | 12/2007 | Sharkey et al. |
| 7,374,530 B2 | 5/2008 | Schaller |
| 7,399,271 B2 | 7/2008 | Khairkhahan et al. |
| 7,431,726 B2 | 10/2008 | Spence et al. |
| 7,452,325 B2 | 11/2008 | Schaller |
| 7,507,252 B2 | 3/2009 | Lashinski et al. |
| 7,582,051 B2 | 9/2009 | Khairkhahan et al. |
| 7,611,534 B2 | 11/2009 | Kapadia et al. |
| 7,704,277 B2 | 4/2010 | Zakay et al. |
| 7,736,388 B2 | 6/2010 | Goldfarb et al. |
| 7,749,249 B2 | 7/2010 | Gelbart et al. |
| 8,128,644 B2 | 3/2012 | Carley et al. |
| 8,348,972 B2 * | 1/2013 | Soltz ............... A61B 17/0644 227/175.1 |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0041915 A1 | 11/2001 | Roue et al. |
| 2001/0044568 A1 | 11/2001 | Langberg et al. |
| 2002/0013621 A1 | 1/2002 | Stobie et al. |
| 2002/0016628 A1 | 2/2002 | Langberg et al. |
| 2002/0026092 A1 | 2/2002 | Buckberg et al. |
| 2002/0055775 A1 | 5/2002 | Carpentier et al. |
| 2002/0082621 A1 | 6/2002 | Schurr et al. |
| 2002/0087173 A1 | 7/2002 | Alferness et al. |
| 2002/0111647 A1 | 8/2002 | Khairkhahan et al. |
| 2002/0115944 A1 | 8/2002 | Mendes et al. |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0169504 A1 | 11/2002 | Alferness et al. |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2002/0198603 A1 | 12/2002 | Buckberg et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078652 A1 | 4/2003 | Sutherland |
| 2003/0078671 A1 | 4/2003 | Lesniak et al. |
| 2003/0083742 A1 | 5/2003 | Spence et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0149333 A1 | 8/2003 | Alferness |
| 2003/0163191 A1 | 8/2003 | Nikolic et al. |
| 2003/0167055 A1 | 9/2003 | Kolata et al. |
| 2003/0220667 A1 | 11/2003 | Van Der Burg et al. |
| 2003/0229395 A1 | 12/2003 | Cox |
| 2004/0002626 A1 | 1/2004 | Feld et al. |
| 2004/0054279 A1 | 3/2004 | Hanley |
| 2004/0127916 A1 | 7/2004 | Bolduc et al. |
| 2004/0133220 A1 | 7/2004 | Lashinski et al. |
| 2004/0133273 A1 | 7/2004 | Cox |
| 2004/0138529 A1 | 7/2004 | Wiltshire et al. |
| 2004/0138744 A1 | 7/2004 | Lashinski et al. |
| 2004/0138745 A1 | 7/2004 | Macoviak et al. |
| 2004/0153146 A1 | 8/2004 | Lashinski et al. |
| 2004/0158321 A1 | 8/2004 | Reuter et al. |
| 2004/0186566 A1 | 9/2004 | Hindrichs et al. |
| 2004/0215232 A1 | 10/2004 | Belhe et al. |
| 2004/0220593 A1 | 11/2004 | Greenhalgh |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0260390 A1 | 12/2004 | Sarac et al. |
| 2004/0260393 A1 | 12/2004 | Rahdert et al. |
| 2004/0267191 A1 | 12/2004 | Gifford, III et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0038509 A1 | 2/2005 | Ashe |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0075727 A1 | 4/2005 | Wheatley |
| 2005/0080402 A1 | 4/2005 | Santamore et al. |
| 2005/0096498 A1 | 5/2005 | Houser et al. |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0131441 A1 | 6/2005 | Iio et al. |
| 2005/0137689 A1 | 6/2005 | Salahieh et al. |
| 2005/0137700 A1 | 6/2005 | Spence et al. |
| 2005/0143809 A1 | 6/2005 | Salahieh et al. |
| 2005/0149014 A1 | 7/2005 | Hauck et al. |
| 2005/0154252 A1 | 7/2005 | Sharkey et al. |
| 2005/0177180 A1 | 8/2005 | Kaganov et al. |
| 2005/0177227 A1 | 8/2005 | Heim et al. |
| 2005/0182365 A1 | 8/2005 | Hennemann et al. |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0197716 A1 | 9/2005 | Sharkey et al. |
| 2005/0209636 A1 | 9/2005 | Widomski et al. |
| 2005/0216052 A1 | 9/2005 | Mazzocchi et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0267573 A9 | 12/2005 | Macoviak et al. |
| 2005/0267574 A1 | 12/2005 | Cohn et al. |
| 2005/0273138 A1 | 12/2005 | To et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0025784 A1 | 2/2006 | Starksen et al. |
| 2006/0025800 A1 | 2/2006 | Suresh |
| 2006/0030881 A1 | 2/2006 | Sharkey et al. |
| 2006/0058871 A1 | 3/2006 | Zakay et al. |
| 2006/0135968 A1 | 6/2006 | Schaller |
| 2006/0135970 A1 | 6/2006 | Schaller |
| 2006/0173536 A1 | 8/2006 | Mathis et al. |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0241334 A1 | 10/2006 | Dubi et al. |
| 2006/0241745 A1 | 10/2006 | Solem |
| 2006/0264980 A1 | 11/2006 | Khairkhahan et al. |
| 2006/0276683 A1 | 12/2006 | Feld et al. |
| 2006/0281965 A1 | 12/2006 | Khairkhahan et al. |
| 2006/0293698 A1 | 12/2006 | Douk |
| 2007/0016068 A1 | 1/2007 | Grunwald et al. |
| 2007/0027533 A1 | 2/2007 | Douk |
| 2007/0050019 A1 | 3/2007 | Hyde |
| 2007/0093869 A1 * | 4/2007 | Bloom ............... A61B 17/0644 606/219 |
| 2007/0118215 A1 | 5/2007 | Moaddeb |
| 2007/0135826 A1 | 6/2007 | Zaver et al. |
| 2007/0156233 A1 | 7/2007 | Kapadia et al. |
| 2007/0161846 A1 | 7/2007 | Nikolic et al. |
| 2007/0185571 A1 | 8/2007 | Kapadia et al. |
| 2007/0198058 A1 | 8/2007 | Gelbart et al. |

(56) References Cited

U.S. PATENT DOCUMENTS

| | | |
|---|---|---|
| 2007/0213578 A1 | 9/2007 | Khairkhahan et al. |
| 2007/0213815 A1 | 9/2007 | Khairkhahan et al. |
| 2007/0219460 A1 | 9/2007 | Goldenberg |
| 2007/0250160 A1 | 10/2007 | Rafiee |
| 2007/0270681 A1 | 11/2007 | Phillips et al. |
| 2007/0270688 A1 | 11/2007 | Gelbart et al. |
| 2007/0270943 A1 | 11/2007 | Solem et al. |
| 2008/0004643 A1 | 1/2008 | To et al. |
| 2008/0004697 A1 | 1/2008 | Lichtenstein et al. |
| 2008/0033541 A1 | 2/2008 | Gelbart et al. |
| 2008/0045778 A1 | 2/2008 | Lichtenstein et al. |
| 2008/0051802 A1 | 2/2008 | Schostek et al. |
| 2008/0071298 A1 | 3/2008 | Khairkhahan et al. |
| 2008/0086164 A1 | 4/2008 | Rowe |
| 2008/0132915 A1 | 6/2008 | Buckman et al. |
| 2008/0133002 A1 | 6/2008 | Gelbart et al. |
| 2008/0140188 A1 | 6/2008 | Rahdert et al. |
| 2008/0177300 A1 | 7/2008 | Mas et al. |
| 2008/0228266 A1 | 9/2008 | McNamara et al. |
| 2008/0262609 A1 | 10/2008 | Gross et al. |
| 2008/0288060 A1 | 11/2008 | Kaye et al. |
| 2009/0076597 A1 | 3/2009 | Dahlgren et al. |
| 2009/0192527 A1 | 7/2009 | Messas |
| 2009/0287304 A1 | 11/2009 | Dahlgren et al. |
| 2009/0318957 A1* | 12/2009 | Viola .............. A61B 17/0644 606/219 |
| 2010/0161047 A1 | 6/2010 | Cabiri |
| 2010/0222789 A1 | 9/2010 | Gelbart et al. |
| 2010/0234886 A1* | 9/2010 | Godin .............. A61B 17/0401 606/219 |
| 2011/0015476 A1* | 1/2011 | Franco .............. A61B 17/0401 600/37 |
| 2011/0022166 A1 | 1/2011 | Dahlgren et al. |
| 2011/0082538 A1 | 4/2011 | Dahlgren et al. |
| 2011/0087203 A1 | 4/2011 | Lichtenstein et al. |
| 2011/0087227 A1 | 4/2011 | Mazur et al. |
| 2011/0301618 A1 | 12/2011 | Lichtenstein |
| 2012/0083806 A1 | 4/2012 | Goertzen |
| 2012/0245604 A1 | 9/2012 | Tegzes |
| 2013/0041405 A1 | 2/2013 | Gelbart et al. |
| 2013/0238089 A1 | 9/2013 | Lichtenstein et al. |
| 2013/0345797 A1 | 12/2013 | Dahlgren et al. |

FOREIGN PATENT DOCUMENTS

| | | |
|---|---|---|
| WO | 03/015611 A2 | 2/2003 |
| WO | 03/077800 A1 | 9/2003 |
| WO | 2004/012629 A1 | 2/2004 |
| WO | 2004/047679 A1 | 6/2004 |
| WO | 2004/084746 A2 | 10/2004 |
| WO | 2004/100803 A1 | 11/2004 |
| WO | 2005/046520 A2 | 5/2005 |
| WO | 2005/070330 A1 | 8/2005 |
| WO | 2005/102181 A1 | 11/2005 |
| WO | 2006/017809 A2 | 2/2006 |
| WO | 2006/135747 A2 | 12/2006 |
| WO | 2006/135749 A2 | 12/2006 |
| WO | 2007/021647 A2 | 2/2007 |
| WO | 2007/115390 A1 | 10/2007 |

OTHER PUBLICATIONS

Mazur et al., "Bone Fixation Device, Tools and Methods", U.S. Appl. No. 61/138,920, filed Dec. 18, 2008, 88 pgs.
Menicanti et al., "The Dor Procedure: What has Changed After Fifteen Years of Clinical Practice?", Journal of Thoracic and Cardiovascular Surgery 124(5):886-890, Nov. 2002.
Otasevic, et al., "First-in-Man Implantation of Left Ventricular Partitioning Device in a Patient With Chronic Heart Failure: Twelve-Month Follow-Up", Journal of Cardiac Failure, vol. 13, No. 7, 2007, pp. 517-520.
Rivera et al., "Ventricular Aneurysms and Akinesis", Cleveland Clinic Quarterly 45(1):133-135, 1978.
Sharkey, et al., "Left Ventricular Apex Occluder. Description of a Ventricular Partitioning Device", EuroIntervention, 2006, 2:125-127.
Stiles, et al., "Simulated Characterization of Atherosclerotic Lesions in the Coronary Arteries by Measurement of Bioimpedance", IEE Transactions on Biomedical Engineering, 50(7):916-921, 2003.
Tanaka, et al., "Artificial SMA Valve for Treatment of Urinary Incontinence: Upgrading of Valve and Introduction of Transcutaneous Transformer", Bio-Medical Materials and Engineering; vol. 9, 1999, pp. 97-112.
Timek, et al., "Septal-Lateral Annular Cinching (SLAC) Reduces Mitral Annular Size Without Perturbing Normal Annular Dynamics", Journal of Heart Valve Disease, vol. 11, No. 1, Jan. 2002; pp. 2-10.
Timek, et al., "Septal-Lateral Annular Cinching Abolishes Acute Ischemic Mitral Regurgitation", Journal of Thoracic and Cardiovascular Surgery, vol. 123, No. 5, May 2002, pp. 881-888.
Torrent-Guasp et al., "Spatial Orientation of the Ventricular Muscle Band and Approach to Partial Ventriculotomy in Heart Failure", Pathogenesis and Treatment, Ch. 36, pp. 685-693, 2002.
Valvano, et al., "Thermal Conductivity and Diffusivity of Biomaterials Measured with Self-Heated Thermistors", International Journal of Thermophysics, vol. 6, No. 3, 1985, pp. 301-311.
Written Opinion, dated Sep. 4, 2009 for PCT/US2009/043612, 6 pgs.
Written Opinion dated Jun. 16, 2011 for PCT/US2010/050945, 4 pgs.
Written Opinion, dated Jan. 8, 2007 for PCT/CA2006/001123, 6 pgs.
Lichtenstein, "Closing Openings in Anatomical Tissue", Amendment filed May 15, 2014 in U.S. Appl. No. 13/112,695, 30 pages.
Lichtenstein, "Closing Openings in Anatomical Tissue", Amendment filed Aug. 8, 2013 in U.S. Appl. No. 13/112,695, 23 pages.
Lichtenstein, "Closing Openings in Anatomical Tissue", Amendment filed Dec. 22, 2014 in U.S. Appl. No. 13/112,695, 16 pages.
Lichtenstein, "Closing Openings in Anatomical Tissue", Office Action dated May 8, 2013 in U.S. Appl. No. 13/112,695, 12 pages.
Lichtenstein, "Closing Openings in Anatomical Tissue", Office Action dated Dec. 4, 2013 in U.S. Appl. No. 13/112,695, 31 pages.
Lichtenstein, "Closing Openings in Anatomical Tissue", Office Action dated Jun. 24, 2014 in U.S. Appl. No. 13/112,695, 17 pages.
Athanasuleas et al, "Surgical Anterior Ventricular Restoration for Ischemic Cardiomyopathy", Operative Techniques in Thoracic and Cardiovascular Surgery 7(2):66-75, May 2002.
Buchbinder, Maurice, "Dynamic Mitral Valve Annuloplasty: A Reshapable Ring for Residual and Recurring MR", Foundation for Cardiovascular Medicine, La Jolla, CA, May 24, 2007, 23 pgs.
Cardiac Implants, URL=http://nmtmedical.com/products/ci/index.htm, download date May 13, 2006, 1 pg.
Cooley, "Ventricular Aneurysms and Akinesis", Cleveland Clinic Quarterly 45(1):130-132, 1978.
Dahlgren et al., "Medical Device, Kit and Method for Constricting Tissue or a Bodily Orifice, for Example a Mitral Valve", U.S. Appl. No. 61/278,232, filed Oct. 1, 2009, 214 pgs.
Dahlgren et al., "Medical Device for Constricting Tissue or a Bodily Orifice, for Example a Mitral Valve", Amendment filed Apr. 13, 2010 for U.S. Appl. No. 12/120,195, 22 pgs.
Dahlgren et al., "Medical Device for Constricting Tissue or a Bodily Orifice, for Example a Mitral Valve", Office Action dated Dec. 18, 2009 for U.S. Appl. No. 12/120,195, 9 pgs.
Dahlgren et al., "Medical Device for Constricting Tissue or a Bodily Orifice, for Example a Mitral Valve", Office Action dated Jul. 7, 2010 for U.S. Appl. No. 12/120,195, 14 pgs.
Dahlgren et al., "Medical Device for Constricting Tissue or a Bodily Orifice, for Example a Mitral Valve", Preliminary Amendment filed Oct. 6, 2010 in U.S. Appl. No. 12/899,407, 8 pgs.
Dahlgren et al, "Medical Device for Constricting Tissue or a Bodily Orifice, for Example a Mitral Valve", Office Action dated Sep. 13, 2012 for U.S. Appl. No. 12/899,407, 10 pgs.
Dahlgren et al, "Medical Device for Constricting Tissue or a Bodily Orifice, for Example a Mitral Valve", Amendment filed Dec. 13, 2012 for U.S. Appl. No. 12/899,407, 22 pages.

(56) References Cited

OTHER PUBLICATIONS

Dahlgren et al, "Medical Device for Constricting Tissue or a Bodily Orifice, for Example a Mitral Valve", Office Action dated Mar. 8, 2013 for U.S. Appl. No. 12/899,407, 11 pages.
Dahlgren et al, "Medical Device for Constricting Tissue or a Bodily Orifice, for Example a Mitral Valve", Amendment filed Aug. 8, 2013 for U.S. Appl. No. 12/899,407, 26 pages.
David et al., "Postinfarction Ventricular Septal Rupture:Repair by Endocardial Patch with Infarct Exclusion", Journal of Thoracic and Cardiovascular Surgery 110(5):1315-1322, 1995.
Dor et al., "Late Hemodynamic Results After Left Ventricular Patch Repair Associated with Coronary Grafting in Patients with Postinfarction Akinetic or Dyskinetic Aneurysm of the Left Ventricle", Journal of Thoracic Cardiovascular Surgery 110(5):1291-1301, 1995.
Dor et al., "Left Ventricular Aneurysm: A New Surgical Approach", Thoracic Cardiovascular Surgery 37:11-19, 1989.
Dor, "Left Ventricular Aneurysms: The Endoventricular Circular Patch Plasty", Seminars in Thoracic and Cardiovascular Surgery 9(2):123-130, Apr. 1997.
Gelbart et al., "Artificial Valve", Amendment filed Jan. 29, 2010 for U.S. Appl. No. 11/497,306, 22 pgs.
Gelbart et al., "Artificial Valve", Office Action dated May 7, 2010 for U.S. Appl. No. 11/497,306, 12 pgs.
Gelbart et al., "Method and Device for Closing Holes in Tissue", Amendment filed Jan. 30, 2009 for U.S. Appl. No. 11/436,585, 5 pgs.
Gelbart et al., "Method and Device for Closing Holes in Tissue", Amendment filed Jun. 2, 2009 for U.S. Appl. No. 11/436,585, 7 pgs.
Gelbart et al., "Method and Device for Closing Holes in Tissue", Amendment filed May 4, 2012 for U.S. Appl. No. 12/777,883, 12 pgs.
Gelbart et al., "Method and Device for Closing Holes in Tissue", Amendment filed Oct. 26, 2009 for U.S. Appl. No. 11/436,585, 13 pgs.
Gelbart et al., "Method and Device for Closing Holes in Tissue", Amendment filed Sep. 22, 2008 for U.S. Appl. No. 11/436,585, 3 pgs.
Gelbart et al., "Method and Device for Closing Holes in Tissue", Office Action dated Feb. 23, 2012 for U.S. Appl. No. 12/777,883, 8 pgs.
Gelbart et al., "Method and Device for Closing Holes in Tissue", Office Action dated Jan. 2, 2009 for U.S. Appl. No. 11/436,585, 11 pgs.
Gelbart et al., "Method and Device for Closing Holes in Tissue", Office Action dated Jul. 7, 2009 for U.S. Appl. No. 11/436,585, 9 pgs.
Gelbart et al., "Method and Device for Closing Holes in Tissue", Office Action dated Sep. 4, 2008 for U.S. Appl. No. 11/436,585, 8 pgs.
Goertzen et al., "Tissue Anchor System", Amendment filed Apr. 29, 2013 for U.S. Appl. No. 13/247,380, 22 pgs.
Goertzen et al., "Tissue Anchor System", Office Action dated Jan. 29, 2013, for U.S. Appl. No. 13/247,380, 10 pages.
Goertzen et al., "Tissue Anchor System", Office Action dated Aug. 13, 2013 for U.S. Appl. No. 13/247,380, 15 pages.
Goertzen et al., "Tissue Anchor System", Amendment filed Oct. 11, 2013 for U.S. Appl. No. 13/247,380, 10 pages.
Goertzen et al., "Tissue Anchor System", Amendment filed Dec. 10, 2013 for U.S. Appl. No. 13/247,380, 11 pages.
International Search Report dated Jan. 8, 2007 for PCT/CA2006/001123, 5 pgs.
International Search Report dated Jun. 16, 2011 for PCT/US2010/050945, 5 pgs.
International Search Report dated Sep. 4, 2009 for PCT/US2009/043612, 7 pgs.
Jatene, "Left Ventricular Aneurysmectomy", Journal of Thoracic and Cardiovascular Surgery 89(3):321-331, 1985.
Konings, et al., "Development of an Intravascular Impedance Catheter for Detection of Fatty Lesions in Arteries", IEEE Transactions on Medical Imaging, vol. 16, No. 4, Aug. 1997, pp. 439-446.
Lichtenstein "Method and Apparatus for Percutaneous Reduction of Anterior-Posterior Diameter of Mitral Valve", Office Action dated Dec. 1, 2008 for U.S. Appl. No. 11/400,260, 10 pgs.
Lichtenstein "Method and Apparatus for Percutaneous Reduction of Anterior-Posterior Diameter of Mitral Valve", Office Action dated May 15, 2006 for U.S. Appl. No. 10/690,131, 9 pgs.
Lichtenstein et al., "Method for Anchoring a Mitral Valve", Amendment filed Aug. 31, 2009 for U.S. Appl. No. 11/475,978, 24 pgs.
Lichtenstein et al., "Method for Anchoring a Mitral Valve", Amendment filed Mar. 26, 2010 for U.S. Appl. No. 11/475,978, 26 pgs.
Lichtenstein et al., "Method for Anchoring a Mitral Valve", Office Action dated Dec. 29, 2009 for U.S. Appl. No. 11/475,978, 7 pgs.
Lichtenstein et al., "Method for Anchoring a Mitral Valve", Office Action dated May 1, 2009 for U.S. Appl. No. 11/475,978, 6 pgs.
Lichtenstein et al., "System for Improving Diastolic Dysfunction", Amendment filed Apr. 22, 2009 for U.S. Appl. No. 11/497,309, 23 pgs.
Lichtenstein et al., "System for Improving Diastolic Dysfunction", Amendment filed Apr. 7, 2010 for U.S. Appl. No. 11/497,309, 8 pgs.
Lichtenstein et al., "System for Improving Diastolic Dysfunction", Amendment filed Oct. 23, 2009 for U.S. Appl. No. 11/497,309, 9 pgs.
Lichtenstein et al., "System for Improving Diastolic Dysfunction", Office Action dated Aug. 5, 2009 for U.S. Appl. No. 11/497,309, 10 pgs.
Lichtenstein et al., "System for Improving Diastolic Dysfunction", Office Action dated Dec. 24, 2008 for U.S. Appl. No. 11/497,309, 8 pgs.
Lichtenstein et al., "System for Improving Diastolic Dysfunction", Office Action dated Jan. 20, 2010 for U.S. Appl. No. 11/497,309, 10 pgs.

* cited by examiner

CLOSING OPENINGS IN ANATOMICAL TISSUE

CROSS REFERENCE TO RELATED APPLICATIONS

This application is a divisional application of U.S. patent application Ser. No. 13/112,695, filed on May 20, 2011, now U.S. Pat. No. 9,050,066, issued on Jun. 9, 2015, which claims benefit under 35 U.S.C. 119(e) to U.S. Provisional Patent Application No. 61/352,277, filed Jun. 7, 2010. The entire disclosure of each of the applications cited in this paragraph is hereby incorporated herein by reference.

TECHNICAL FIELD

This disclosure is generally related to surgery and in particular to closing openings in tissue during minimally invasive surgery. For example, this disclosure may be particularly useful for closing openings left by catheters during percutaneous surgical procedures such as minimally invasive cardiac surgery and other surgeries requiring access to anatomical cavities.

BACKGROUND

More and more surgical procedures are performed percutaneously by the use of catheter delivered devices. The main advantages are faster patient recoveries and lower costs to the medical system. Some tissues, such as muscular tissue or arterial walls, do not seal well and are sometimes subject to blood pressure, thereby requiring an immediate haemostatic seal to close an opening in the tissue. Conventional solutions typically rely on various forms of plugs, such as expanding foam plugs, and expanding metal plugs to close the opening.

One disadvantage of plugs is that in order to form a good seal they apply forces to the opening that tend to cause the opening to become larger, rather than the more natural way which is to contract the opening in order to promote healing. A conventional device that functions by contracting the opening is the Star Closure device sold by Abbott Vascular (www.abbottvasculardevices.com). This closure device is however only suitable for thin walled body tissues as it relies on folding the tissue. When sealing larger openings in thicker tissue the gripping points employed to pull the tissue inwards have to be spread over an area significantly larger than the opening size, similar to what is done in traditional suturing. Attaching the closure device in close proximity to the opening does not allow sufficient forces to be applied, therefore creating a marginal closure.

An additional shortcoming of prior art solutions for closing openings in thicker muscular tissue such as heart wall tissue is that the inner surfaces of the heart are irregular in form. When inserting a closure device into an inner surface of the heart, the reliability of the closure is heavily dependent on the angle of the puncture relative to the angle of the inner heart surface.

An additional shortcoming of closure devices employing piercing gripping elements includes occurrences of tissue tearing which can negatively impact the reliability and efficacy of these devices.

There is a need for improved closure systems and methods for closing an opening to an anatomical cavity, the closure systems being deliverable by a catheter to an inside tissue surface of an anatomical cavity.

There is a need for improved closure systems and methods for closing an opening to an anatomical cavity, the closure systems being capable of adapting to differences in the angle of the interior surface within the anatomical cavity relative to an orientation of the opening.

There is a need for improved closure systems and methods for closing an opening to an anatomical cavity, the closure systems being capable of distributing the closure forces to an interior surface of the anatomical cavity to reduce occurrences of localized tissue tearing.

BRIEF SUMMARY

The present design of a medical system for closing at least one opening leading to an anatomical cavity is disclosed. In one embodiment, the medical system includes a device sized for passage through an opening in a tissue wall leading to an anatomical cavity. The device includes an elongated member that includes a proximal portion and a distal portion, the elongated member arranged for insertion into the anatomical cavity, distal portion first. The elongated member further includes a bending portion positioned between the proximal portion and the distal portion, the bending portion allowing for articulated movement between the distal and the proximal portions of the elongated member. The device includes an orientation control unit sized for insertion into the anatomical cavity. The orientation control unit includes a member having a contact surface that is positionable to contact an interior tissue surface within the anatomical cavity. The orientation control unit is operable for changing an orientation of the distal portion relative to proximal portion. The orientation control unit may be operable for changing the orientation of the distal portion relative to the proximal portion upon establishing contact between the contact surface and the tissue surface within the anatomical cavity. The orientation control unit may be further operable for reducing an angular deviation of the distal portion from an axis positioned normal to a point on the interior tissue surface within the anatomical cavity.

The elongated member may be moved along a first direction to insert the distal portion into the anatomical cavity. The orientation control unit may be further operable for changing the orientation of the distal portion relative to the proximal portion when the elongated member is moved along a second direction opposite to the first direction. A spacing between the orientation control unit and the bending portion may be predetermined to position a bending point of the bending portion at least proximate to the interior tissue surface within the anatomical cavity when the orientation control unit is operated to change the orientation of the distal portion relative to the proximal portion. A spacing between the orientation control unit and the bending portion may be predetermined to position a bending point of the bending portion in the anatomical cavity when the orientation control unit is operated to change the orientation of the distal portion relative to the proximal portion. The interior tissue surface within the anatomical cavity can include a port of the opening and the contact surface of the orientation control unit may contact a region of the interior tissue surface within the anatomical cavity at least proximate to the port of the opening.

The contact surface may assume a retracted position during a movement of the orientation control unit through the opening. The contact surface may further assume an extended position during an operation of the orientation control unit to contact the interior tissue surface within the anatomical cavity. A fluid source fluidly coupled to the orientation control unit may be selectively controlled to position the contact surface between the retracted position and the extended position. The orientation control unit may include an inflatable member. The contact surface may be provided by a portion of the inflatable member. The inflatable member may include an annular shaped inflatable member.

The distal portion of the elongated member may include an instrument configured to modify a portion of an interior tissue surface within the anatomical cavity. The distal portion may include a clip configured to constrict a portion of the opening, the clip being releasably coupled to the device. The clip may include at least two piercing elements, each of the at least two piercing elements arranged to pierce a portion of the tissue wall proximate to the opening. An inflatable member may be positioned between the at least two piercing elements, and a fluid source coupled to the inflatable member may be selectively controlled to expand the inflatable member to increase a spacing between the at least two piercing elements. The fluid source may also be selectively controlled to contract the inflatable member to cause the at least two piercing elements to pinch at least a portion of the interior tissue surface within the anatomical cavity comprising a port of the opening. The inflatable member may be positioned between the at least two piercing elements to prevent a pointed portion of each piercing element from extending beyond a surface of the inflatable member when the fluid source is selectively controlled to expand the inflatable member.

Each of the at least two piercing elements may pierce through the tissue wall, and a capping member may be provided to secure a portion of each of the at least two piercing elements protruding from the tissue wall. A hub that includes a bio-absorbable material may be provided to couple each of the at least two piercing elements together. A spacing between the clip and the bending portion may be predetermined to position a bending point of the bending portion between the at least two piercing elements. A perforating member that forms the opening in the tissue wall may also be provided. A tubular member may be positioned in the opening and the elongated member may be sized for passage through the tubular member positioned in the opening. The bending portion may be a substantially unconstrained bending portion arranged to freely bend during the changing of the orientation of the distal portion relative to proximal portion by the orientation control unit. The orientation control unit may be positioned between the bending portion and the distal portion. The opening may extend through the tissue wall along a path having a direction that is skewed relative to the interior tissue surface within the anatomical cavity.

A medical system may be summarized as including a device sized to pass through an opening in a tissue wall leading to an anatomical cavity. The device includes an elongated member that includes a proximal portion and a distal portion, the elongated member arranged to be inserted distal portion first into the anatomical cavity. The device further includes a bending portion positioned between the proximal portion and the distal portion, the bending portion allowing the proximal and the distal portions to articulate with respect to one another. The device further includes an orientation control unit that is inserted into the anatomical cavity. The orientation control unit is operable for defining an orientation of a portion of an interior tissue surface within the anatomical cavity and aligning the distal portion of the elongated member to the interior tissue surface within the anatomical cavity in accordance with the defined orientation of the interior tissue surface within the anatomical cavity. The orientation control unit may be operable for aligning the distal portion of the elongated member to the interior tissue surface within the anatomical cavity to reduce an angular deviation of the distal portion of the elongated member from an axis positioned normal to a point on the portion of the interior tissue surface within the anatomical cavity. The orientation control unit may include a member having a contact surface arranged to contact the interior tissue surface within the anatomical cavity to define the orientation of the interior tissue surface within the anatomical cavity. The interior tissue surface within the anatomical cavity can include a port of the opening. The bending portion may be a substantially unconstrained bending portion arranged to freely bend during the aligning of the distal portion of the elongated member to the interior tissue surface within the anatomical cavity by the orientation control unit. The opening can extend through the tissue wall along a path having a direction that is skewed relative to the interior tissue surface within the anatomical cavity.

Another medical system may be summarized as including a device sized for passage through an opening in a tissue wall leading to an anatomical cavity. The device includes an elongated member that includes a proximal portion and a distal portion, the elongated member arranged to be advanced distal portion first into the anatomical cavity. The device includes a bending portion positioned between the proximal portion and the distal portion, the bending portion allowing the proximal and the distal portions to articulate with respect to one another. The device includes a clip releasably coupled to the elongated member, the clip configured to constrict a portion of the opening. The device further includes an orientation control unit that is insertable into the anatomical cavity. The orientation control unit includes a member having a contact surface positionable to contact an interior tissue surface within the anatomical cavity to define an orientation of a portion of the interior tissue surface within the anatomical cavity. The orientation control unit is operable to change an orientation of the distal portion of the elongated member relative to proximal portion of the elongated member to align the clip with the portion of the interior tissue surface within the anatomical cavity. The clip includes at least two piercing elements, each of the at least two piercing elements arranged to pierce a portion of the tissue wall proximate to the opening. An inflatable member may be provided to adjust a spacing between the at least two piercing elements. The opening can extend through the tissue wall along a path having a direction that is skewed relative to the interior tissue surface within the anatomical cavity.

A method for constricting an opening may be summarized as including providing an orientation control unit and a clip. Each of the orientation control unit and the clip are advanced through the opening into an anatomical cavity. The method includes defining an orientation of an interior tissue surface within the anatomical cavity by establishing contact between a contact surface of a member of the orientation control unit and a portion of the interior tissue surface within the anatomical cavity. The method includes aligning the clip based at least on the defined orientation of the portion of the interior tissue surface within the anatomical cavity and constricting a portion of the opening with the aligned clip.

The method may include defining the orientation of portion of the interior tissue surface within the anatomical cavity simultaneously with the aligning of the clip. The orientation control unit may be pivotally coupled to an elongated member, and the method may include moving the elongated member along a first direction through the opening to advance the orientation control unit into the anatomical cavity and moving the elongated member along a second direction opposite to the first direction to establish the contact between the contact surface and the interior tissue surface within the anatomical cavity.

The contact surface of the member employed by the method may assume a retracted position during the advancing of the orientation control unit through the opening. The contact surface further may assume an extended position during the establishing of the contact between the contact surface and the interior tissue surface within the anatomical cavity such that a portion of the contact surface in the extended position extends beyond a perimeter of a port of the opening.

The clip employed by the method may include at least two piercing elements, each of the at least two piercing elements arranged to pierce a portion of the tissue wall proximate to the opening. The method may include increasing a spacing between the at least two piercing elements when the clip is positioned within the anatomical cavity. An inflatable member positioned between the at least two piercing elements can be provided, and the method may include inflating the inflatable member to increase the spacing between the at least two piercing elements when the clip is positioned in the anatomical cavity. The inflatable member may be deflated to cause the at least two piercing elements to pinch at least a portion of the interior tissue surface within the anatomical cavity that includes a port of the opening. The opening can extend through the tissue wall along a path having a direction that is skewed relative to the interior tissue surface within the anatomical cavity.

A medical system for closing one or more openings, each of the one or more openings leading to an anatomical cavity may be summarized as including a device sized to pass through a first opening of the one or more openings into the anatomical cavity. The device includes a constricting unit arranged to be delivered into the anatomical cavity at a position proximate to an interior tissue surface within the anatomical cavity to constrict a portion of an opening located on the interior tissue surface within the anatomical cavity. The device further includes an occluding member arranged to be delivered into the anatomical cavity at a position between the constricting unit and the interior tissue surface within the anatomical cavity, the occluding member blocking the constricted portion of the opening located on the interior tissue surface within the anatomical cavity.

The medical system may include an elongated member, a portion of the elongated member sized to pass through the first opening into the anatomical cavity. Each of the constricting unit and the occluding member may be releasably coupled to the elongated member. The elongated member may be moveable along a first direction to insert the constricting unit and the occluding member into the anatomical cavity. The constricting unit may be further operable for constricting the portion of the opening located on the interior tissue surface within the anatomical cavity when the elongated member is moved along a second direction opposite to the first direction. The opening located on the interior tissue surface within the anatomical cavity can be the first opening, and the constricting unit may be further operable for constricting the portion of the first opening when the elongated member is moved along the second direction to position a portion of the elongated member away from the portion of the first opening. The medical system may include a tubular member and the elongated member may be sized to pass through the tubular member positioned in the first opening. The constricting unit may further constrict the portion of the first opening when the tubular member is moved along the second direction to position a portion of the tubular member away from the portion of the first opening.

The constricting unit may constrict the portion of the opening located on the interior tissue surface within the anatomical cavity by engaging a plurality of regions of the interior tissue surface within the anatomical cavity and drawing the plurality of regions together, each of the regions located at least proximate to a port of the opening located on the interior tissue surface within the anatomical cavity. The occluding member may include an inflatable member. The inflatable member may include a flexible membrane that is selectively moveable between an extended position and a retracted position. A portion of the flexible membrane may block the constricted portion of the opening located on the interior tissue surface within the anatomical cavity. A portion of the flexible membrane may block the constricted portion of the opening located on the interior tissue surface within the anatomical cavity when the flexible membrane is positioned in the retracted position.

The constricting unit may include a clip arranged to constrict the portion of the opening located on the interior tissue surface within the anatomical cavity. The clip may include at least two piercing elements, each of the at least two piercing elements arranged to pierce the interior tissue surface within the anatomical cavity at least proximate to the opening located on the interior tissue surface within the anatomical cavity. The occluding member may include an inflatable member that is fluidly coupled to a fluid source. The inflatable member may be positioned between the at least two piercing elements, and the fluid source may be selectively controlled to expand the inflatable member to increase a spacing between the at least two piercing elements. The fluid source may also be selectively controlled to contract the inflatable member to cause the at least two piercing elements to pinch at least a portion of the interior tissue surface within the anatomical cavity that includes a port of the opening located on the interior tissue surface within the anatomical cavity. A portion of the contracted inflatable member may block the constricted portion of the opening located on the interior tissue surface within the anatomical cavity. The inflatable member may be positioned between the at least two piercing elements to restrict a pointed portion of each piercing element from extending beyond a surface of the inflatable member. The inflatable member may be an annular inflatable member. A conduit may be provided for coupling the fluid source to the inflatable member, and the inflatable member may be releasably coupled to the conduit. A hub that includes a bio-absorbable material may be provided to couple each of the at least two piercing elements together. A perforating member may be provided for forming at least one opening of the one or more openings in a tissue wall surrounding a portion of the anatomical cavity. The constricting unit may capture the occluding member when the occluding member is positioned between the constricting unit and the interior tissue surface within the anatomical cavity. The opening located on the interior tissue surface within the anatomical cavity can be the first opening.

Another medical system may be summarized as including a device sized to pass through an opening to an anatomical cavity. The opening extends through a tissue wall to an interior tissue surface within the anatomical cavity. The device includes an elongated member, a portion of the elongated member sized for insertion into the anatomical cavity. The device includes a clip releasably coupled to the elongated member, the clip arranged to be inserted into the anatomical cavity at a position at least proximate to the interior tissue surface within the anatomical cavity, and the clip being further arranged to constrict a portion of the opening. The device further includes an inflatable member releasably coupled to the elongated member. The inflatable member is arranged to be inserted into the anatomical cavity at a position between the clip and the interior tissue surface within the anatomical cavity. The inflatable member includes a flexible membrane. The medical system further includes a fluid source fluidly coupled to the inflatable member, the fluid source being selectively controllable for moving the flexible membrane between a retracted position and an extended position.

The inflatable member may be positioned to block the constricted portion of the opening when the flexible membrane is moved from the extended position to the retracted position. The clip may include at least two piercing elements, each of the at least two piercing elements arranged to pierce a portion of the tissue wall at least proximate to the opening. The inflatable member may increase a spacing between the at least two piercing elements when the flexible membrane is moved from the retracted position to the extended position. The clip may pinch a portion of the interior tissue surface within the anatomical cavity comprising a port of the opening when the flexible membrane is moved from the extended position to the retracted position.

A method for closing one or more openings, each of the one or more openings leading to an anatomical cavity may be summarized as including providing a constricting unit and an occluding member and advancing each of the constricting unit and the occluding member through a first opening of the one or more openings into the anatomical cavity. The method includes positioning each of the constricting unit and the occluding member in the anatomical cavity at a position at least proximate to an interior tissue surface within the anatomical cavity. The method includes constricting a portion of an opening located on the interior tissue surface within the anatomical cavity with the constricting unit, and blocking the constricted portion of the opening located on the interior tissue surface within the anatomical cavity with the occluding member. The method may include positioning the occluding member between the constricting unit and the interior tissue surface within the anatomical cavity.

The method may include capturing the occluding member between the constricting unit and the constricted portion of the opening. The opening located on the interior tissue surface within the anatomical cavity can be the first opening. The constricting unit can be coupled to an elongated member, and the method may include moving the elongated member along a first direction through the first opening to advance the constricting unit into the anatomical cavity and moving the elongated member along a second direction opposite to the first direction while constricting the portion of the first opening with the constricting unit.

The constricting unit may constrict the portion of the opening located on the interior tissue surface within the anatomical cavity by engaging a plurality of regions of the interior tissue surface within the anatomical cavity and drawing the plurality of regions together, each of the regions being located proximate to a port of the opening located on the interior tissue surface within the anatomical cavity. The occluding member can include an inflatable member that includes a flexible membrane that is selectively moveable between a retracted position and an extended position, and the method may further include blocking the constricted portion of the opening located on the interior tissue surface within the anatomical cavity when the flexible membrane is in the retracted position.

The constricting unit can include a clip that includes at least two piercing elements, each of the at least two piercing elements arranged to pierce the interior tissue surface within the anatomical cavity at a location proximate to the opening located on the interior tissue surface within the anatomical cavity. The method may include decreasing a spacing between the at least two piercing elements to constrict the portion of the opening located on the interior tissue surface within the anatomical cavity. A hub comprising a bioabsorbable material can be provided to couple each of the at least two piercing elements together. An inflatable member can be provided between the at least two piercing elements, and the method may include inflating the inflatable member to increase a spacing between the at least two piercing elements when the clip is positioned in the anatomical cavity. The inflatable member may be deflated to cause the at least two piercing elements to pinch at least a portion of the interior tissue surface within the anatomical cavity that includes a port of the opening located on the interior tissue surface within the anatomical cavity. The method may include forming at least one opening of the one or more openings with a perforating member.

A medical system for closing one or more openings, each of the one or more openings leading to an anatomical cavity may be summarized as including a device sized to pass through a first opening of the one or more openings into the anatomical cavity. The device includes a closure unit arranged to be delivered into the anatomical cavity at a position proximate to an interior tissue surface within the anatomical cavity. The closure unit is arranged to close an opening of the one or more openings located on the interior tissue surface within the anatomical cavity. The device further includes an intermediate member arranged to be inserted into the anatomical cavity at a position between the closure unit and the interior tissue surface within the anatomical cavity. The closure unit includes at least one piercing element, each of the at least one piercing element arranged to pierce through the intermediate member into the interior tissue surface within the anatomical cavity.

The medical system may include an elongated member, a portion of the elongated member sized to pass through the first opening into the anatomical cavity. Each of the closure unit and the intermediate member may be releasably coupled to the elongated member. The elongated member may be moved along a first direction to insert the closure unit and the intermediate member into the anatomical cavity. The closure unit may be further operable for closing the opening located on the interior tissue surface within the anatomical cavity when the elongated member is moved along a second direction opposite to the first direction.

The closure unit may close the opening located on the interior tissue surface within the anatomical cavity by constricting a portion of the opening located on the interior tissue surface within the anatomical cavity. The closure unit may constrict the portion of the opening located on the interior tissue surface within the anatomical cavity by engaging a plurality of regions of the interior tissue surface within the anatomical cavity and drawing the plurality of regions together, each of the regions being located at least proximate to a port of the opening located on the interior tissue surface within the anatomical cavity.

The intermediate member may include an absorbent material. The intermediate member may include a pledget. The intermediate member may include an inflatable portion that includes a flexible membrane that is selectively moveable between a retracted position and an extended position. Each of the at least one piercing elements may be arranged to pierce through the intermediate member into the interior tissue surface within the anatomical cavity when the flexible membrane is positioned in the extended position. The intermediate member may include a non-inflatable portion. The inflatable portion may selectively move the non-inflatable portion, and each of the at least one piercing elements may be arranged to pierce through the non-inflatable portion into the interior tissue surface within the anatomical cavity when the flexible membrane is positioned in the extended position. The non-inflatable portion may be positioned around a perimeter of the inflatable portion. The at least one piercing element may include a plurality of piercing elements and the non-inflatable portion may be part of a plurality of non-inflatable portions such that each non-inflatable portion corresponds to a respective one of the piercing elements. The medical system may include an inflatable member and a fluid source fluidly coupled to the inflatable portion. The at least one piercing element may include a plurality of piercing elements that are arranged such that the inflatable member is positioned between the plurality of piercing elements. The fluid source may be selectively controlled to expand the inflatable member to increase a spacing between the plurality of piercing elements. The fluid source may be selectively controlled to contract the inflatable member to cause the at least two piercing elements to pinch at least a portion of the interior tissue surface within the anatomical cavity comprising a port of the opening located on the interior tissue surface within the anatomical cavity. The inflatable member may be positioned between the plurality of piercing elements to prevent a pointed portion of each piercing element from extending beyond a surface of the inflatable member when the fluid source is controlled to expand the inflatable portion. The inflatable member may include an annular inflatable portion. A conduit may be provided for coupling the fluid source to the inflatable member, and the inflatable member may be releasably coupled to the conduit. A hub that includes a bio-absorbable material may be provided to couple each of the piercing elements together.

A perforating member may be provided to form at least one opening of the one or more openings in a tissue wall surrounding a portion of the anatomical cavity. A perforating member may be provided to form the first opening in a tissue wall surrounding a portion of the anatomical cavity. A tubular member may be positioned in the first opening with the elongated member sized to pass through the tubular member positioned in the first opening. The opening located on the interior tissue surface within the anatomical cavity can be the first opening.

A medical system may be summarized as including a device sized to pass through an opening to an anatomical cavity, the opening extending through a tissue wall to an interior tissue surface within the anatomical cavity. The device includes an elongated member, a portion of the elongated member sized to be inserted into the anatomical cavity. The device includes a clip releasably coupled to the elongated member, the clip arranged to be inserted into the anatomical cavity at a position at least proximate to the interior tissue surface within the anatomical cavity. The clip is further arranged to constrict a portion of the opening. The device further includes an intermediate member releasably coupled to the elongated member, the intermediate member arranged to be inserted into the anatomical cavity at a position between the clip and the interior tissue surface within the anatomical cavity. The clip includes at least two piercing elements, each of the at least two piercing elements arranged to pierce through the intermediate member into the interior tissue surface within the anatomical cavity.

The medical system may include an inflatable member releasably coupled to the elongated member. The inflatable member is sized to be inserted into the anatomical cavity and includes a flexible membrane. The medical system may include a fluid source that is coupled to the inflatable member. The fluid source is selectively operable for moving the flexible membrane between a retracted position and an extended position. Each of the at least two piercing elements may be arranged to pierce through the intermediate member into the interior tissue surface within the anatomical cavity when the flexible membrane is positioned in the extended position. The clip may be arranged to pinch at least a portion of the interior tissue surface within the anatomical cavity that includes a port of the opening when the flexible membrane is moved from the extended position to the retracted position. The intermediate member may include an absorbent material.

A method for closing one or more openings, each of the one or more openings leading to an anatomical cavity may be summarized as including providing a constricting unit that includes at least one piercing element. The method further includes providing an intermediate member. Each of the constricting unit and the intermediate member are advanced through a first opening of the one or more openings into the anatomical cavity. The method includes positioning each of the constricting unit and the intermediate member in the anatomical cavity at a position at least proximate to an interior tissue surface within the anatomical cavity. The method further includes constricting a portion of an opening located on the interior tissue surface within the anatomical cavity with the constricting unit, and piercing the intermediate member with each of the at least one piercing element.

The method may include positioning the intermediate member between the constricting unit and the interior tissue surface within the anatomical cavity. The method may include capturing the intermediate member between the constricting unit and the interior tissue surface within the anatomical cavity. The method may include piercing through the intermediate member into the interior tissue surface within the anatomical cavity with each of the at least one piercing element. The opening located on the interior tissue surface within the anatomical cavity can be the first opening and the constricting unit may be coupled to an elongated member. The method may further include moving the elongated member along a first direction through the first opening to advance the constricting unit into the anatomical cavity and moving the elongate member along a second direction opposite to the first direction while constricting the portion of the first opening with the constricting unit.

The constricting unit may be arranged to constrict the portion of the opening located on the interior tissue surface within the anatomical cavity by engaging a plurality of regions of the interior tissue surface within the anatomical cavity and drawing the plurality of regions together, each of the regions being located at least proximate to a port of the opening located on the interior tissue surface within the anatomical cavity. The method may include providing an inflatable member that includes a flexible membrane that is selectively moveable between a retracted position and an extended position. The method may include piercing the intermediate member with each of the at least one piercing element when the flexible membrane is positioned in the extended position.

The at least one piercing element can include at least two piercing elements, and the method may include decreasing a spacing between the at least two piercing elements to pinch at least a portion of the interior tissue surface within the anatomical cavity that includes a port of the opening located on the interior tissue surface within the anatomical cavity. The method may include providing an inflatable member positioned between the at least two piercing elements, and inflating the inflatable member to increase a spacing between the at least two piercing elements when the constricting unit is positioned in the anatomical cavity. The method may include deflating the inflatable member while pinching the at least a portion of the interior tissue surface within the anatomical cavity that includes the port of the opening located on the interior tissue surface within the anatomical cavity. The method may include forming at least one of the one or more openings with a perforating member. The opening located on the interior tissue surface within the anatomical cavity can be the first opening.

Various systems and methods may include combinations and subsets of those summarized above.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements may be arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various embodiments of the invention. However, one skilled in the art will understand that the invention may be practiced without these details. In other instances, well-known structures have not been shown or described in detail to avoid unnecessarily obscuring descriptions of the disclosed embodiments.

Figure 1:
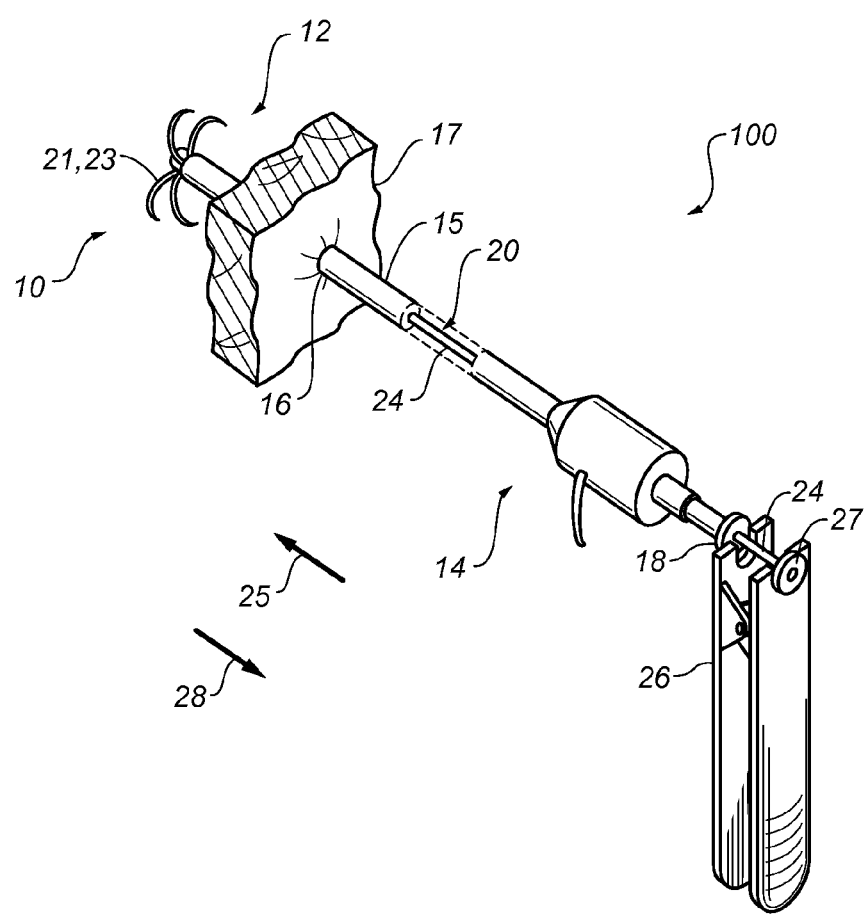
FIG. 1 is an isometric view of a medical system including a closure device according to an example embodiment.

Referring to FIG. 1, a medical system 100 including a closure device 10 according to an example embodiment is inserted into an anatomical cavity 12 such a cavity in the heart via catheter 14. A tubular member 15 is shown inserted into a first opening 16 that leads through a tissue wall 17 to anatomical cavity 12. In this example embodiment first opening 16 has been formed in tissue wall 17 with a perforating member or instrument (not shown). Various perforating members can be used to form first opening 16 in tissue wall 17. For example, puncturing members such as trocars are commonly employed to form openings in tissue walls. Without limitation, other forms of perforating methods including cutting, ablation, and irradiation techniques can be employed by various embodiments.

Catheter 14 employs a seal (not shown) allowing insertion and removal of various instruments and devices without much blood loss. This is well known in the art of minimally invasive surgery. When the surgical procedure is completed and first opening 16 needs to be closed, tubular member 15 allows for the passage of closure device 10 through first opening 16 into anatomical cavity 12. In this example embodiment, closure device 10 includes an elongated member 20. In this example embodiment, elongated member 20 includes a closure unit 21 and a rod member 24 sized for providing closure unit 21 into anatomical cavity 12 via passage through tubular member 15 along a first direction 25. Both rod member 24 and tubular member 15 have respective flanges 27 and 18 allowing a pulling tool 26 to exert a significant pulling force on rod member 24 relative to tubular member 15. In this regard, pulling tool 26 is arranged to pull rod member 24 through tubular member 15 along a second direction 28 that is opposite to first direction 25 in a manner similar to that taught in commonly assigned U.S. patent application Ser. No. 11/436,585 which is herein incorporate by reference. Pulling tool 26 may be made of plastic or metal, plastic being preferred if tool is to be disposable. Rod member 24 and tubular member 15 are preferably made of stainless steel. In this example embodiment closure unit 21 is adapted for constricting a portion of first opening 16. In this example embodiment closure unit 21 includes clip 23. In various other embodiments, closure unit 21 may include alternate and/or additional elements or members.

Figure 2A:
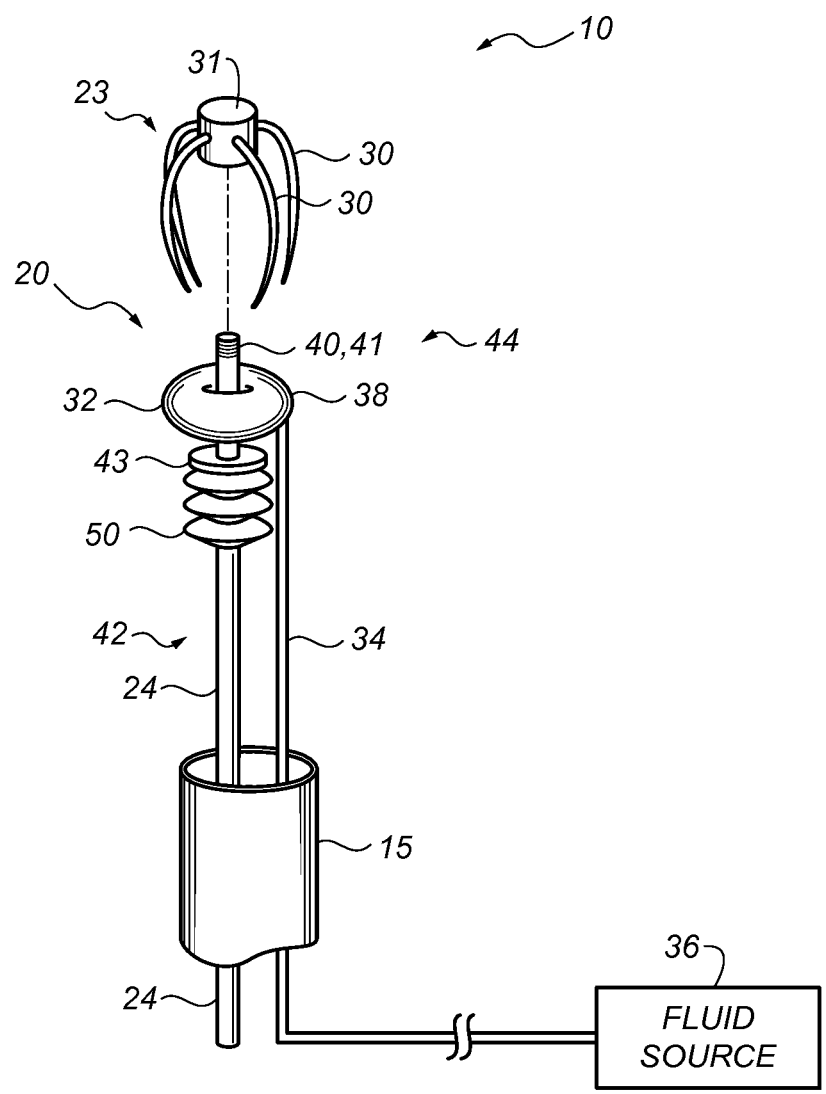
FIG. 2A is a partially exploded schematic view of a portion of closure device of an example embodiment.
Figure 2B:
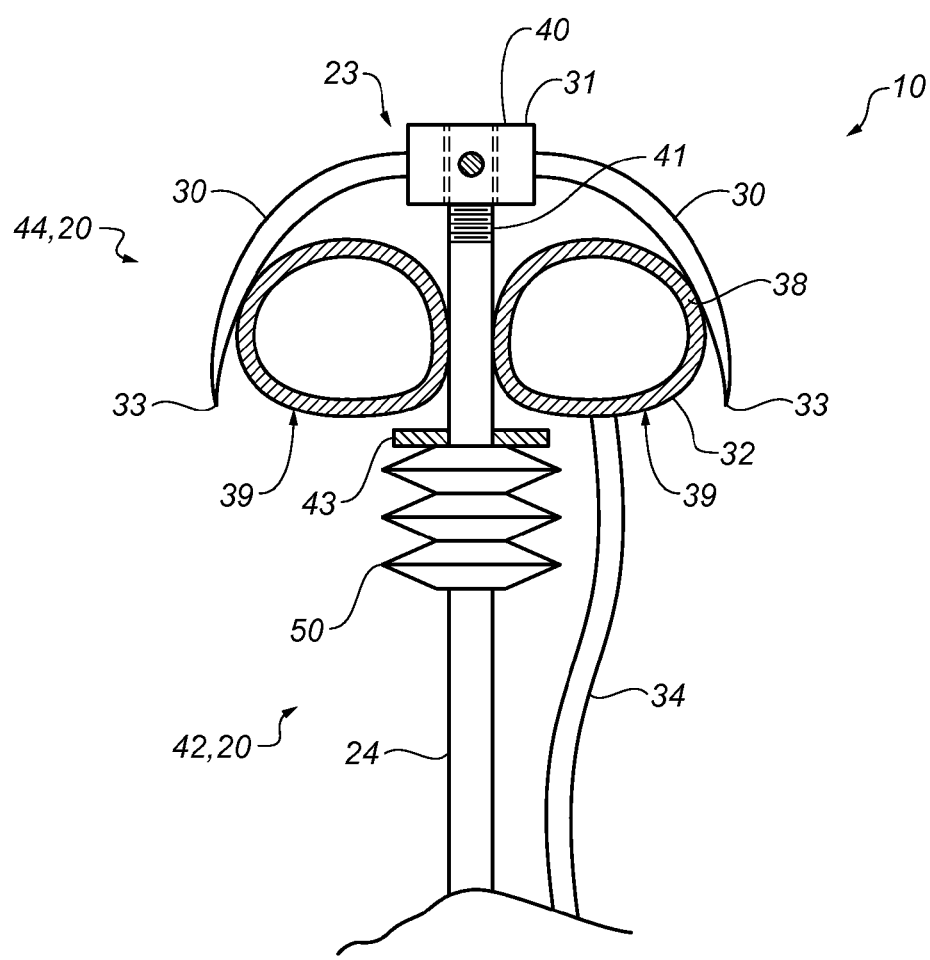
FIG. 2B is a schematic sectional view of a portion of the closure device of FIG. 2A.

FIG. 2A is schematic a partially exploded view of a portion of closure device 10. FIG. 2B is a schematic sectional view of a portion of the closure device 10 of FIG. 2A. FIGS. 2C to 2G show a sequence of operations employing the closure device 10 of FIG. 2A as per a method according to an example embodiment.

As shown in FIG. 2A, clip 23 includes various piercing elements 30 arranged to engage a surface of anatomical cavity 12. (i.e., not shown in FIG. 2A). In this example embodiment, each piercing element 30 is arranged to pierce a portion of tissue wall 17 (not shown in FIG. 2A) that defines a portion of anatomical cavity 12. In this example embodiment, four (4) piercing elements 30 are employed, although it is understood that other suitable number of piercing elements 30 can be employed in other example embodiments. The number of piercing elements 30 can vary in accordance with a particular closure method that is employed by a given example embodiment. For example, when first opening 16 is to be closed by constricting a portion of first opening 16, at least two piecing elements can be employed. In this case, each of the at least two piercing elements 30 is employed to pinch at least a portion of the interior tissue surface within the anatomical cavity 12 including a port of the first opening 16. In this example embodiment, each of the at least two piercing elements 30 is employed to pinch at least a portion of tissue wall 17 that includes first opening 16. In some example embodiments, at least one piercing element 30 can be employed to pierce a portion of the interior tissue surface within the anatomical cavity 12 proximate a port of the first opening 16.

In this example embodiment, each piercing element 30 is made of Nitinol, a highly flexible Nickel Titanium alloy well known in the art of medical devices. Since the elastic range of Nitinol is about ten times larger than steel, clip 23 can be made formed into a sufficiently small initial configuration adapted passage through tubular member 15. It is noted that in some example embodiments, the initial configuration can accommodate minor amounts of interference with the interior surface of tubular member 15 since clip 23 typically includes sufficient compliance to accommodate this interference. Care should however be maintained to reduce the generation of debris that may arise from frictional effects generated during the passage of clip 23 through tubular member 15. In this example embodiment, expansion forces can be applied to clip 23 when it is position within anatomical cavity 12 to cause clip 23 to assume a configuration suitable for gripping a portion of tissue wall 17 over an area significantly larger than the area of a port of first opening 16. When the expansion forces are removed, clip 23 tries to return to its natural (relaxed) shape, which covers a significantly smaller area, pulling the tissue with it and forming an instant haemostatic seal.

In this example embodiment, closure device 10 includes an inflatable member 32 positioned between clip 23 and rod member 24 as best seen in FIG. 2A and FIG. 2B. Inflatable member 32 can include various suitable expansion members including bladders and balloons by way of non-limiting example. In this example embodiment, inflatable member 32 is coupled to a fluid source 36 via conduit 34. In this example embodiment, conduit 34 passes through tubular member 15. In this example embodiment, conduit 34 is shown as a separate member from rod member 24. In other example embodiments, conduit 34 and rod member 24 can be integrated into a single assembly. For example, conduit 34 can take the form of a passageway within rod member 24.

In this example embodiment, fluid supply 36 is selectively controllable to provide a suitable pressurized fluid to inflatable member 32 via conduit 34. A suitable fluid such as a saline solution that is commonly used in the art may be used to inflate inflatable member 32. In this example embodiment, inflatable member 32 includes a flexible membrane 38 that is adapted from moving between a retracted position to an extended position in accordance the selective control of fluid source 36. In this example embodiment, the contracted position corresponds to deflated state of inflatable member 32 whereas the extended position corresponds to an inflated state of inflatable member 32. It is understood that these positions can be adjusted to suit in accordance with the selective application of fluid that is provided to inflatable member 32. In some example embodiments, inflatable member 32 is sized too large to be advanced through first opening 16 in the extended position. Fluid source 36 can include by way of non-limiting example, a supply of pressurized fluid, various valves and various regulators adapted for selectively supplying fluid with a desired characteristic such a particular pressure value. As shown in FIG. 2B, inflatable member 32 is positioned between the piercing elements 30 of clip 23. Flexible membrane 38 is shown positioned in the extended position in FIG. 2B. This positioning of flexible membrane 38 has caused a spacing between piercing elements 30 to increase. As shown in FIG. 2B, inflatable member 32 is positioned between piercing elements 30 to help reduce occurrences of a pointed portion 33 of each piercing element 30 from extending beyond a surface 39 of flexible membrane 38 when flexible membrane 38 is in the extended position. This positioning can be employed to help reduce occurrences in which piercing elements 30 inadvertently engage a surface or other structure in anatomical cavity 12.

In this example embodiment, inflatable member 32 is annular in form and is positioned proximate to a coupling 40 of elongated member 20. In this example embodiment, coupling 40 includes a threaded end 41 that is provided for threaded attachment with a hub 31 of clip 23. Hub 31 is arranged to physically coupling each of piercing elements 30 together. In this example embodiment, coupling 40 allows clip 23 to be releasably coupled to elongated member 20. It is understood that coupling 40 is not limited to threaded couplings and other suitable couplings can be employed in other example embodiments.

In this example embodiment, elongated member 20 includes a bending portion 50. In this example embodiment, bending portion 50 is positioned between a distal portion 44 of elongated member 20 that includes at least clip 23 and inflatable member 32 and a proximal portion 42 of elongated member 20 that includes at least rod member 24. In some example embodiments, distal portion 44 includes an instrument adapted for modifying a portion of an interior tissue surface within the anatomical cavity 12. Bending portion 50 allows for a relative articulated movement between distal portion 44 and proximal portion 42. Bending portion 50 allows for a relative swinging movement between distal portion 44 and proximal portion 42. Bending portion 50 allows distal portion 44 to be reoriented relative to proximal portion 42. Without limitation, bending portion 50 can include various bending members such as a jointed or flexible hinge member, an articulated joint that includes various segments united by joints or flexures or a flexible coupling that includes a discrete or an infinite number of bending points. In this example embodiment, bending portion 50 is employed to pivotally couple distal portion 44 to proximal portion 42. In this example embodiment, bending portion 50 allows for threaded end 41 to rotate about its axis. In this example embodiment, bending portion 50 enables elongated member 20 to have both torsional and axial stiffness, while allowing for rotation as described above. In this example embodiment, bending portion 50 allows distal portion 44 to pivot relatively to proximal portion 42 in three dimensional space. In this example embodiment, bending portion 50 is an unconstrained bending portion adapted to freely bend. In this example embodiment, bending portion 50 is sized for passage through tubular member 15 into anatomical cavity 12.

Figure 2C:
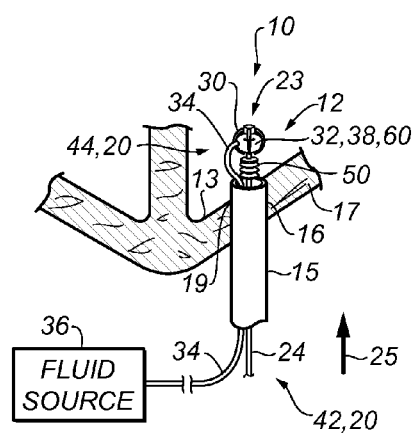
FIGS. 2C to 2G is a schematic representation of a sequence of operations employing the closure device of FIG. 2A according to an example embodiment.

FIG. 2C shows a positioning of clip 23 and inflatable member 32 within anatomical cavity 12 after a passage through tubular member 15 positioned in first opening 16 in tissue wall 17. In this example embodiment, flexible membrane 38 is positioned in the retracted position during the passage of inflatable member 32 through tubular member 15. In this embodiment, rod member 24 was advanced along first direction 25 to position these members within anatomical cavity 12.

Figure 2D:
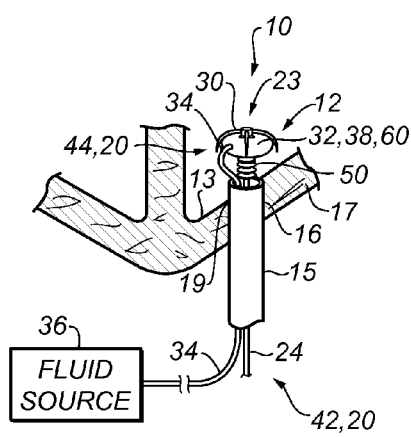

As shown in FIG. 2D, when the clip 23 has passed through opening 16 via tubular member 15 and is inside the anatomical cavity 12, fluid source 36 is selectively controlled to cause inflatable member 32 to inflate and cause the flexible membrane 38 to move to its extended position. The movement of flexible membrane 38 in turn increases a spacing between the piercing elements 30 of clip 23. The movement of flexible membrane 38 imparts spring energy in piercing elements 30. In this example embodiment, inflatable member 32 is employed to cause clip 23 to expand to a position referred to as a deployment-ready position.

As shown in FIGS. 2C, 2D, 2E, 2F and 2G, anatomical cavity 12 is defined by various interior tissue surfaces. In this example embodiment, first opening 16 extends through tissue wall 17 along a path having a direction that is skewed relative to interior tissue surface 13 within anatomical cavity 12. In this example embodiment, first opening 16 extends through tissue wall 17 along a path having a direction that obliquely intersects a portion of interior tissue surface 13. In this example embodiment, interior tissue surface 13 includes a port 19 of first opening 16. It is noted that that interior tissue surface 13 can be skewed relative to opening 16 in three dimensional space. Surfaces such as interior tissue surface 13 having skewed orientations relative to first opening 16 can create difficulties in employing a closure device, especially one that employs a clip. For example, it is noted that if clip 23 as oriented in FIG. 2D were to be brought into contact with obliquely oriented interior tissue surface 13, not all of the piercing elements 30 would be correctly positioned for proper engagement with interior tissue surface 13. In this example embodiment, it is desired that fluid supply 36 be operated to cause a deflation of inflatable member 30 to reduce a spacing between the piercing elements 30 to constrict a portion of first opening 16. If each of the piercing elements 30 is not properly positioned for the required engagement with interior tissue surface 13, the effectiveness of the pinching action provided by piercing elements 30 may become compromised. It is understood that the amount of skew associated with a surface such as interior tissue surface 13 can vary from patient to patient or from medical procedure to medical procedure. In some cases, surface orientations having little or substantially no skew may be encountered while in other cases, surface orientations having pronounced skew (i.e. acute angles) may be encountered.

In this example embodiment, closure device 10 includes an orientation control unit 60 which is also sized for insertion into anatomical cavity 12 via tubular member 15 positioned in first opening 16. In this example embodiment, orientation control unit 60 includes a contact surface arranged to contact interior tissue surface 13. In this example embodiment, the contact surface of orientation control unit 60 is provided by surface 39 of flexible membrane 38. Surface 39 is herein referred to as contact surface 39. In this example embodiment contact surface 39 is provided when flexible membrane 38 is moved to its extended position.

In this example embodiment, orientation control unit 60 is operable for changing an orientation of distal portion 44 relative to proximal portion 42. In this example embodiment, orientation control unit 60 is operable for changing an orientation of distal portion 44 relative to proximal portion 42 upon establishing contact between contact surface 39 and interior tissue surface 13. In some example embodiments, orientation control unit 60 is operable to cause bending portion 50 to bend.

Figure 2E:
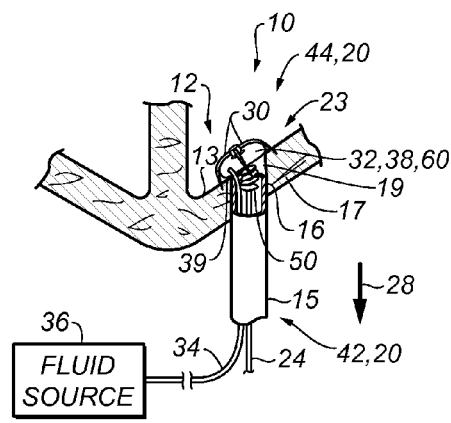

In this example embodiment, after clip 23 has been expanded with the assistance of inflatable member 32, the expanded clip 23 and contact surface 39 are retracted by rod member 24 which is advanced along second direction 28 as shown in FIG. 2E. In this example embodiment, the retraction of rod member 24 along second direction 28 causes a portion of contact surface 39 to come into contact with interior tissue surface 13. Upon further retraction of rod member 24 along second direction 28, orientation control unit 60 causes a change in the orientation of distal portion 44 relative to proximal portion 42. In this example embodiment, a retraction of tubular member 15 along second direction 28 is also made. In this example embodiment, tubular member 15 is retracted at least enough to allow contact surface 39 to contact interior tissue surface 13. It is noted that for clarity, a portion of tubular member 15 has been sectioned to show bending portion 50 in FIGS. 2E and 2F.

As can be seen in FIG. 2E, the further retraction of rod member 24 and the initially contacted portion of contact surface 39 cause distal portion 44 to pivot until contact is established between a remaining portion of contact surface 39 and interior tissue surface 13. In this example embodiment, orientation control unit 60 is operable for reducing an angular deviation of distal portion 44 from an axis (not shown) positioned normal to a point on interior tissue surface 13. In this example embodiment, orientation control unit 60 is operable for defining an orientation of interior tissue surface 13 and aligning distal portion 44 in accordance with the defined orientation. In this example embodiment, orientation control unit 60 is operable for defining an orientation of interior tissue surface 13 simultaneously with the aligning of distal portion 44 in accordance with the defined orientation. In this example embodiment, orientation control unit 60 forms a portion of a self-aligning mechanism employed to align distal portion 44 to interior tissue surface 13. In this example embodiment, the self aligning mechanism includes bending portion 50.

As shown in FIG. 2E, clip 23 is oriented generally normal to the obliquely oriented interior tissue surface 13. Accordingly, each of the piercing elements 30 is correctly positioned for proper engagement with interior tissue surface 13. Orientation control unit has advantageously helped to correctly orient clip 23 so that it can be subsequently deployed correctly into interior tissue surface 13, with all piercing elements 30 being deployed in substantially equal proportion. It is understood that orientation control unit 60 is not limited to the illustrated embodiments. Those skilled in the art will quickly understand that orientation control unit 60 can include other forms of elements operable for defining an orientation of a skewed interior tissue surface 13 and orienting distal portion 44 in accordance with the defined orientation. Without limitation, orientation control units 60 employed in various embodiments can include actively controlled elements including suitable drives and actuators as well as passive elements that are each positionable within an anatomical cavity to define an orientation of a skewed interior tissue surface 13 and/or to orient distal portion 44 in accordance with the defined orientation. Without limitation, contact surface 39 can include a contact surface other than a surface provided by inflatable member 32.

Figure 2F:
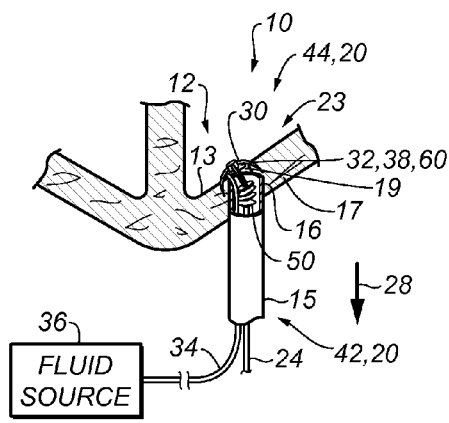

As shown in FIG. 2F, when the clip 23 has been correctly positioned by orientation control unit 60, clip 23 is deployed into a portion of tissue wall 17 by further retracting rod member 24 along second direction 28 and by operating fluid source 36 to deflate inflatable member 32. Deflating inflatable member 32 causes flexible membrane 38 to move towards its retracted position and reduce a spacing between the piercing elements 30. In this regard, clip 23 engages a plurality of regions of interior tissue surface 13 and applies a pinching force suitable for drawing the plurality of regions together, each of the regions being located proximate to port 19. By keeping tension on rod member 24 and deflating inflatable member 32, clip 23 will deploy in a manner where each of the piercing elements 30 will apply pinching forces to a portion the tissue wall 17 (i.e. including a portion of interior tissue surface 13) as the piercing elements are drawn into tissue wall 17 to constrict a portion of first opening 16. Since orientation control unit 60 has oriented clip 23 substantially normal to interior tissue surface 13, a robust anchoring of the clip 23 into the tissue wall 17 can be advantageously achieved.

In some example embodiments, the combination of retracting rod member 24 along second direction 28 and the deflation of inflatable member 32 to deploy piercing elements 30 into tissue wall 17 may require a lateral repositioning of rod member 24 and bending portion 50 within tubular member 15 to fully achieve full penetration of each of the piercing elements 30. In some example embodiments, one or more of rod member 24, bending portion 50 and tubular member 15 are appropriately sized to provide sufficient clearance to accommodate a lateral repositioning of rod member 24 and bending portion 50. This clearance can reduce occurrences of undesired moments being applied to clip 23 during its deployment into tissue wall 17.

In this example embodiment, a spacing between the orientation control unit 60 and the bending portion 50 is predetermined to position a bending point of bending portion 50 proximate to interior tissue surface 13 when orientation control unit 60 is operated to change the orientation of distal portion 44 relative to proximal portion 42. In some example embodiments, bending portion 50 is positioned in anatomical cavity 12 rather than first opening 16 when orientation control unit 60 is operated to change the orientation of distal portion 44 relative to proximal portion 42. In some example embodiments, a spacing between the orientation control unit 60 and the bending portion 50 is predetermined to position a bending point of bending portion 50 in anatomical cavity 12 when orientation control unit 60 is operated to change the orientation of distal portion 44 relative to proximal portion 42. In some example embodiments, bending portion 50 or a bending point of bending portion 50 is positioned between piercing elements 30. In some example embodiments, bending portion 50 includes a virtual pivot point about which an orientation of distal portion 44 can change with respect to proximal portion 42. In some example embodiments, bending portion includes a virtual pivot point that is positioned between piercing elements 30. These example embodiments can be employed to reduce a magnitude of any undesired moment applied to clip 23 during its deployment into tissue wall 17. These example embodiments may be suitable if interior space constraints of tubular member 50 limit lateral positioning of elongated member 20 with tubular member 15 during the deployment of clip 23 into tissue wall 17.

Figure 2G:
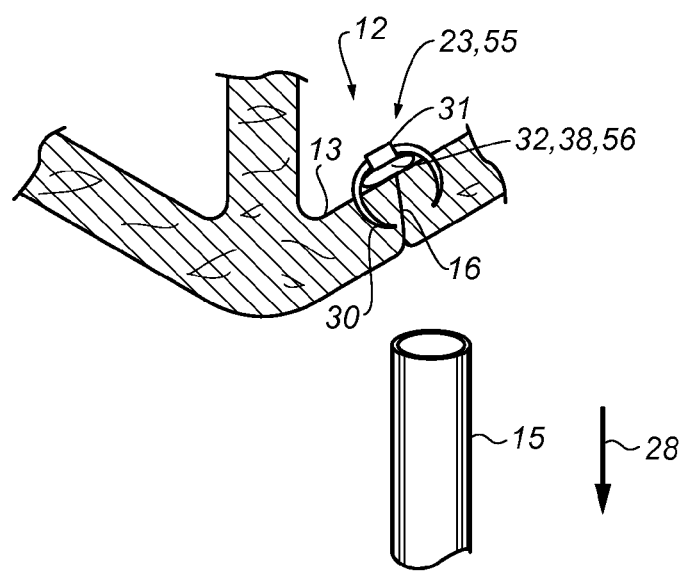

As shown in FIG. 2G, tubular member 15 has been retracted from first opening 16 to position an end portion of tubular member 15 away from a portion of first opening 16 as the piercing elements 30 are deployed into tissue wall 17. The retraction of tubular member 15 allows a portion of first opening 16 to contract and decrease in diameter under the pinching action of piercing elements 30 thereby constricting the portion of first opening 16. The pinching forces applied by clip 23 are able to affect the decrease of diameter of the first opening 16 in tissue wall 17 as clip 23 returns close to its natural shape. It is noted that some degree of inherent spring energy can be maintained within clip 23. When inflatable member 32 has been fully deflated, clip 23 will be fully deployed into tissue wall 17. At this point, it is possible to use angiogram or other visual technique to confirm that first opening 16 has been closed and haemostasis has been achieved. If it has not, inflatable member 32 can be re-inflated and rod member 24 can be repositioned to un-deploy clip 23 and allow the operating physician another opportunity to close first opening 16.

Once haemostasis has been confirmed, rod member 24 can be rotated to disengage threaded end 41 from the hub 31 of clip 23, and a remaining portion of elongated member 20 may be pulled out from the constricted portion of first opening 16 to allow for a further constriction of first opening 16. The elastic compliance provided by the piercing elements 30 of clip 23 allow for the removal of a remaining portion of elongated member 20 from the constricted portion of first opening 16. In some example embodiments, the extraction of rod member 24 is also accompanied by the extraction of inflatable member 32 and conduit 34. In some example embodiments, the extraction of rod member 24 also causes the extraction of inflatable member 32 and conduit 34. In some example embodiments, at least one of inflatable member 32 and conduit 34 is extracted separately from rod member 24. For example, inflatable member 32 can be securely affixed to conduit 34 with a coupling that provides sufficient strength to allow an extraction of conduit 34 to also result in an extraction of inflatable member 32. In these example embodiments, the deflated state of inflatable member 32 is predetermined to be adequately sized to allow for passage through the constricted portion of first opening 16. Again, the elastic compliance provided by the piercing elements 30 of clip 23 is predetermined to allow for the extraction of deflated inflatable member 32.

As shown in FIG. 2G, inflatable member 32 is not extracted from the anatomical cavity 12 in this example embodiment. Rather both clip 23 and inflatable member 32 remain within anatomical cavity 12 after the remaining portion of elongated member 20 has been extracted. In this example inflatable member 32 is releasably coupled to each of rod member 24 and conduit 34 in a manner suitable for allowing inflatable member 32 to remain within anatomical cavity 12 upon their extraction. For example, inflatable member 32 can be slidably coupled to threaded end 41. A flange 43 (shown in FIGS. 2A and 2B) or other abutment can be incorporated to maintain a coupling between inflatable member 32 and threaded end 41 when rod member 15 is advanced along first direction 25. However, when threaded end 41 is unscrewed from hub 31 and rod member 24 is retracted along second direction 28, inflatable member 32 becomes separated from threaded end 41. Conduit 41 can be released from inflatable member 32 with a break away coupling that separates upon the application of a predetermined force to conduit 34.

Figure 2H:
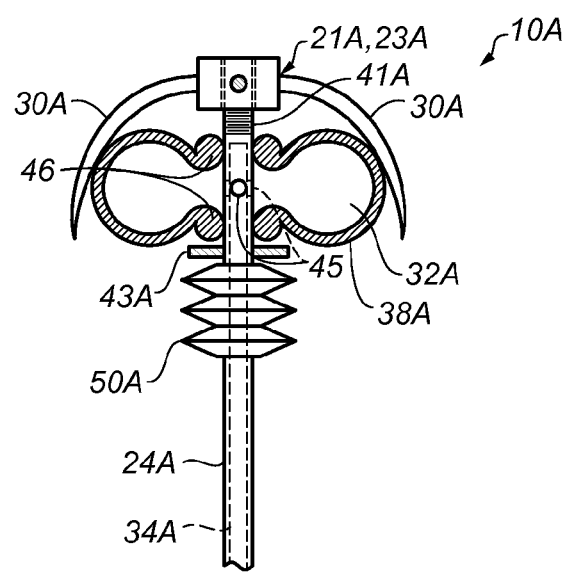
FIG. 2H is a schematic detailed view of a portion of a closure device according to another example embodiment.

FIG. 2H shows a schematic detailed view of a portion of a closure device 10A according to another example embodiment. In this example embodiment, a conduit 34A is provided integrally within a rod member 24A, a bending portion 50A and a threaded end 41A. Ports 45 provide fluid communication between conduit 34A and inflatable member 32A which includes a flexible membrane 38A that is selectively moveable between a retracted position and an extended position. Sealing portions 46 of inflatable member 32A seal against threaded end 41A. In this example embodiment, inflatable member 32A is captured between flange 43A and a closure unit 21A. Closure unit 21A includes a clip 23A which includes a plurality of piercing elements 30A. Clip 23A is releasably coupled to threaded end 41A via a threaded coupling. When threaded end 41A is unscrewed from clip 23A, threaded end 41A can be retracted from inflatable member 32A which can be left behind in an anatomical cavity 12. It is noted that other suitable couplings can be employed to couple with clip 23A in other example embodiments. Flexible membrane 38A is shown in the extended position under the influence of a fluid (not shown) provided through conduit 34A.

Referring back to FIG. 2G, inflatable member 32 is shown positioned between clip 23 and interior tissue surface 13. In this example embodiment, the deployed piercing elements 30 act to capture inflatable member 32 between clip 23 and interior tissue surface 13. For safety and to prevent embolization of inflatable member 32, inflatable member 32 can be coupled with hub 31. In this example embodiment, closure device 10 includes a constricting unit 55 (i.e. clip 23) and an occluding member 56 (i.e. inflatable member 32), both of which are employed to close first opening 16 from within anatomical cavity 12. As shown in FIG. 2G, constricting unit 55 (i.e. clip 23) constricts a portion of first opening 16 while occluding member 56 (i.e. inflatable member 32) blocks the constricted portion of first opening 16. In this example embodiment, a portion of flexible membrane 38 is employed to block the constricted portion of first opening 16. In this example embodiment, a portion of flexible membrane 38 is employed to block the constricted portion of first opening 16 when flexible membrane 38 is positioned in the retracted position.

In this example embodiment, inflatable member 32 is employed as one example of an occluding member 56 that is positioned to additionally block the constricted portion of first opening 16 to advantageously enhance the efficacy of the closure of first opening 16. In some example embodiments, an occluding member 56 including an absorbent material is employed. In some example embodiments, an occluding member 56 including an element adapted for providing a mendicant to the constricted portion of first opening 16 is employed. In some example embodiments, an occluding member 56 including Dacron® or other material that has sealing capabilities is employed. In some example embodiment, an occluding member 56 includes a bio-absorbable material. It is understood the constricting units 55 and occluding members 56 are not limited to clip 23 and inflatable member 32 respectively in various other embodiments. Without limitation, other suitable constricting members 55 and occluding members 56 can be employed in other embodiments.

Figure 3A:
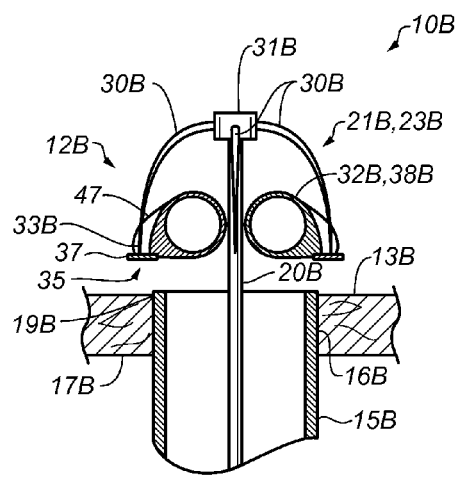
FIG. 3A is a schematic sectional view of a device according to an example embodiment, the device including a closure unit, an intermediate member and an inflatable member in a retracted state.
Figure 3B:
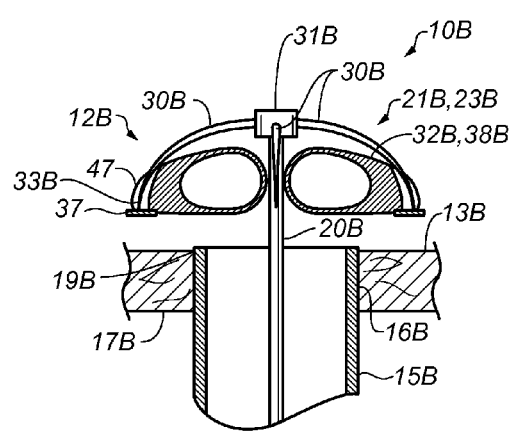
FIG. 3B is a schematic sectional view of the device of FIG. 3A with the inflatable member in an extended state.
Figure 3C:
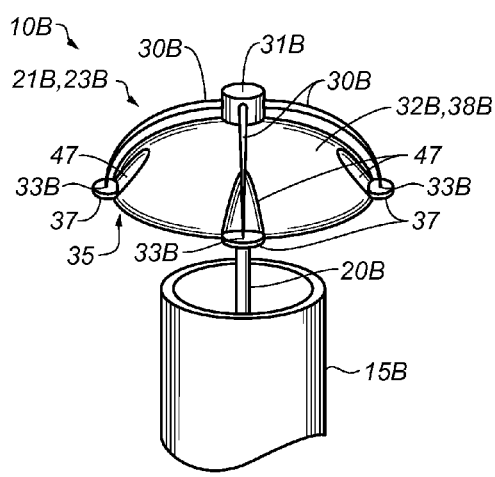
FIG. 3C is an isometric view of the device of FIG. 3A with the inflatable member in an extended state.

FIGS. 3A, 3B and 3C are various views of a portion of a closure device 10B that is insertable into anatomical cavity 12B via a tubular member 15B positioned in a first opening 16B that leads to anatomical cavity 12B. In this example embodiment, closure device 10B includes a closure unit 21B that is operable to constrict a portion of first opening 16B provided in tissue wall 17B. In this example embodiment, closure unit 21B includes a clip 23B. Clip 23B and an inflatable member 32B are operated to constrict a portion of the first opening 16B in a manner similar to other example embodiments described in the present specification. In this example embodiment, closure unit 21B is operable to constrict a portion of the first opening 16B that includes a portion of an interior tissue surface 13B of the anatomical cavity 12B that includes a port 19B of the opening 16B. Clip 23B includes a plurality of piercing elements 30B coupled together by a hub 31B. Hub 31B is releasably coupled via a threaded coupling to an elongated member 20B arranged to insert closure unit 21B through first opening 16B into anatomical cavity 12B.

FIG. 3A is a schematic sectional view of inflatable member 32B in a deflated or retracted state and FIG. 3B shows a sectional view of inflatable member 32B in an inflated or extended state. FIG. 3C is an isometric view of inflatable member 32B in an extended state. In this example embodiment, inflatable member 32B include a flexible membrane 38B that is selectively moveable between a retracted position (i.e., shown in FIG. 3A) and an extended position (i.e., shown in FIG. 3B) under a selective application of a fluid (not shown). Flexible membrane 38B is arranged to adjust a spacing between the piercing elements 30B of clip 23B in a manner similar to that described in other example embodiments. In this example embodiment, inflatable member 32B is also employed during the deployment of clip 23 B to constrict a portion of first opening 16B in a manner similar to that described in other example embodiments. In this example embodiment, closure device 10B includes an intermediate member 35 that is positionable between the closure unit 21B (i.e. clip 23B) and interior tissue surface 13B. In this example embodiment, intermediate member 35 includes a plurality of pads 37 that are positionable between clip 23B and interior tissue surface 13B. In this example embodiment, at least one of the piercing elements 30B is arranged to pierce through a pad 37. In this example embodiment, at least one of the piercing elements 30B is arranged to pierce through a pad 37 into interior tissue surface 13B. In some example embodiments, pads 37 are pierced prior to the deployment of piercing elements 30B into interior tissue surface 13 B to constrict a portion of opening 16B. In some example embodiments, pads 37 are pierced during the deployment of piercing elements 30B into interior tissue surface 13B to constrict a portion of opening 16B.

In this example embodiment, each of the pads 35 corresponds to a respective one of the piercing elements 30B. As best shown in FIG. 3C, each pad 35 is positioned in a pocket 47 provided in inflatable member 32B to locate each pad 37 relative to a respective one of piercing elements 30B in this example embodiment. Other example embodiments may include other arrangements between an intermediate member 35 and a piercing member 30B. For example, a single pad 37 can be positioned to be pierced by at least two of piercing elements 30B. An annular shaped intermediate member 35 can be positioned to be pierced by all of the piercing elements 30B.

In this example embodiment, each of the pads 37 of intermediate member 35 is positioned around a perimeter of flexible membrane 38B. In this example embodiment, each pad 37 of intermediate member 35 is positioned to be pierced by a piercing element 30B when the flexible membrane 38B is moved to an extended position. In this example embodiment, inflatable member 32B provides the intermediate member 35. In this regard, intermediate member 35 includes an inflatable portion (i.e., flexible membrane 38B) and a non-inflatable portion (i.e., pads 37). In this example embodiment the non-inflatable portion is positionable to a location where it can be pierced by a piercing element 30B.

In some example embodiments, pads 37 are employed to reduce occurrences in which pointed portions 33B of the piercing elements 30B can catch or damage anatomical features or structures in anatomical cavity 12B prior to the deployment of piercing elements 30B into interior tissue surface 13B. In some example embodiments, intermediate member 35 is employed as a reinforcement member to distribute the puncturing pressure as piercing elements 30B are deployed into interior tissue surface 13B. This is particularly beneficial when the integrity of the pierced underlying tissue has been compromised from factors such as disease or advanced age. In some example embodiments, intermediate member 35 acts as a pledget. In some example embodiments, intermediate member 35 is employed to promote healing. Without limitation, intermediate member 35 can include one or more of an absorbent material, a bio-absorbable material, and an elastic material. Without limitation, intermediate member 35 can be employed to apply a mendicant to interior tissue surface 13B.

In this example embodiment, each of closure unit 21B and intermediate member 35 are releasably coupled to the elongated member 20B and remain within anatomical cavity 12B in a manner similar to that described in other example embodiments. It is understood that closure unit 21B is not restricted to constricting units. In some example embodiments, closure unit 21B can include an occluding member or blocking member arranged to block a portion of first opening 16B from within anatomical cavity 12B. In various example embodiments, a closure unit 21B and an intermediate member 35 are inserted into anatomical cavity 12B and positioned proximate to interior tissue surface 13B of anatomical cavity 12B. At least one piercing element 30B is also provided to pierce intermediate member 35. In some example embodiments, at least one piercing element 30B can be employed to anchor intermediate member 35 to interior tissue surface 13B. In some example embodiments, at least one piercing element 35B can be employed to anchor closure unit 21B to interior tissue surface 13B.

Figure 4:
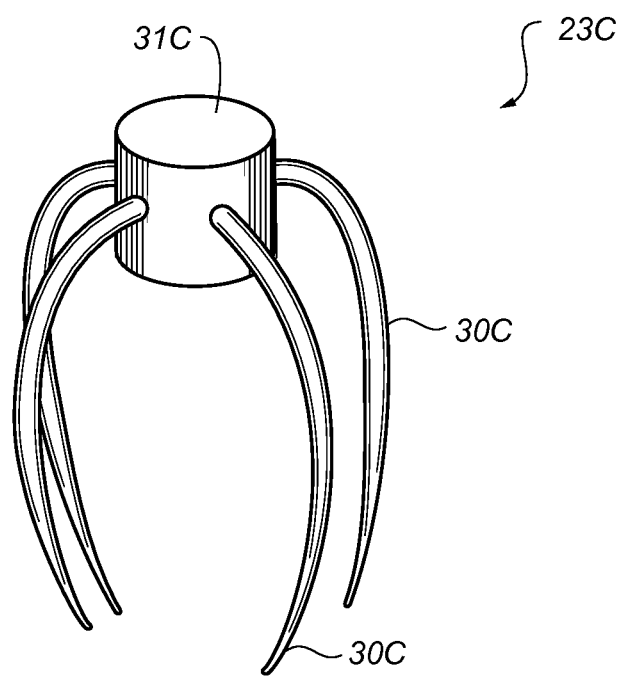
FIG. 4 is an isometric view of a clip employed in an example embodiment.

FIG. 4 is an isometric view of a clip 23C employed in an example embodiment. Clip 23C includes a hub 31C and a plurality of piercing elements 30C. In this example embodiment, hub 31C includes a bio-absorbable material, such as a synthetic co-polymer. In some embodiments, hub 31C is formed around the piercing elements 30C. In other example embodiments, hub 31C includes a plurality of openings adapted for accepting the protrusion of piercing elements 30C therethrough. In some example embodiments, hub 31C is releasably and reversibly coupled to an elongated member 20 (not shown) which is employed for the deployment and possible extraction of clip 23C from a tissue wall 17 of an anatomical cavity 12. When piercing elements 30C are embedded into tissue as per various example embodiments, hub 31C will serve to exert force on the piercing elements 30C to drive them into the tissue. Once clip 23C has been deployed and haemostasis is achieved, hub 31C will be absorbed into the tissue, leaving only the piercing elements 30C remaining in the tissue. This feature is advantageous in reducing the overall footprint of the remaining components in the tissue, thereby reducing obstructions that can impact potential future procedures at the same or surrounding location.

Figure 5:
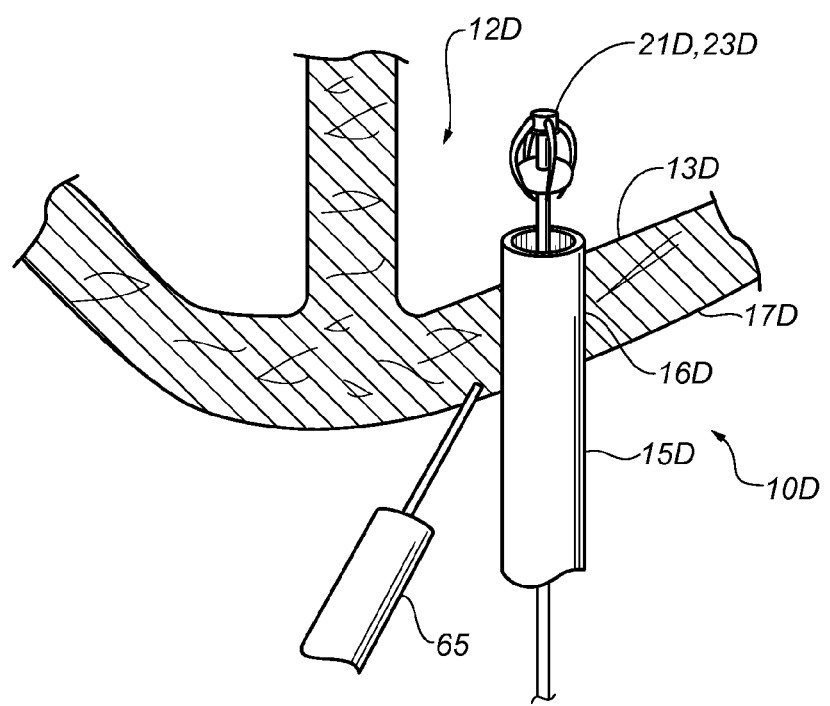
FIG. 5 is a cross-sectional view of a closure device as per another example embodiment.

FIG. 5 is a cross-sectional drawing of a closure device 10D as per another example embodiment. In this example embodiment, tubular member 15D is utilized to deliver a closure unit 21D to an interior tissue surface 13D of an anatomical cavity 12D in manner similar to that described in other example embodiments. In this example embodiment, closure unit 21D includes a clip 23D arranged to constrict a portion of first opening 16D. In some example embodiments, closure unit 21D may include an occluding member. In addition to the closing action of closure unit 21D, applicator 65 is used to deliver an injection of a material (e.g. collagen) that acts to locally swell or expand the cells around the first opening 16D in the tissue wall 17D. This injection can occur slightly before or during the delivery of closure unit 21D. Another variant of this example embodiment can use a bio-adhesive suitable for cardiovascular applications that is applied into the closure in tissue wall 17D after tubular member 15D has been removed to help in sealing first opening 16D. The use of this system in conjunction with closure methods described in other example embodiments can provide a more effective seal during the closure procedure with resulting improvements in short and long-term haemostasis.

Figure 6A:
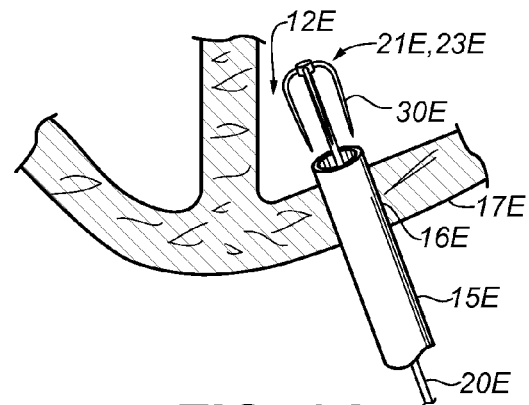
FIGS. 6A, 6B and 6C are schematic representations of various stages of a closing of a first opening in an anatomical cavity as per another example embodiment.
Figure 6B:
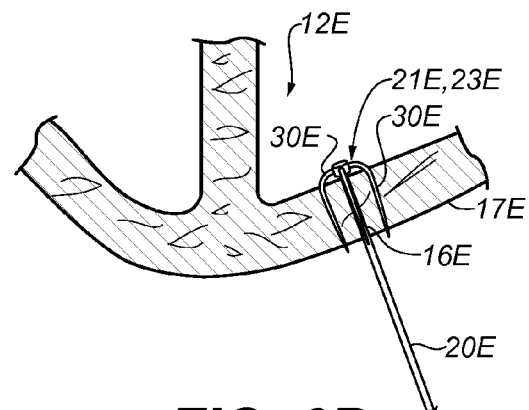
Figure 6C:
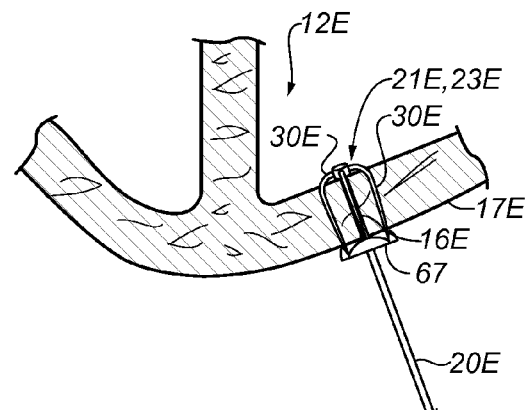

FIGS. 6A, 6B and 6C are schematic representations of various stages of a closing of a first opening 16E in an anatomical cavity 12E as per another example embodiment. As shown in FIG. 6A, tubular member 15E is utilized to deliver a closure unit 21 E through first opening 16E that is provided in a tissue wall 17E that surrounds a portion of anatomical cavity 12E. In this example embodiment, closure unit 21E includes a clip 23E that is arranged to constrict a portion of first opening 16E in a manner similar to that described in other example embodiments. Clip 23E is coupled to elongated member 20E.

As best shown in FIG. 6B, clip 23E includes a plurality of piercing elements 30E that are sized to extend beyond an outer surface of tissue wall 17E into which they are to be deployed. In this regard, the piercing elements 30E are arranged to pierce through tissue wall 17E. FIG. 6B shows that clip 23E has been fully deployed into tissue wall 17E, and a portion of first opening 16E has been constricted after tubular member 15E has been retracted from first opening 16E.

In FIG. 6C, a capping member 67 positioned outside of tissue wall 17E in proximity to the portions of piercing elements 30E which protrude from tissue wall 17E. Capping member 67 includes various elements (not shown) adapted for coupling with the protruding portions of piercing elements 30E. Capping member 67 additionally secures clip 23E to tissue wall 17E thereby further promoting closure of opening 16E and reducing occurrences of clip 23E losing its purchase with tissue wall 17E. The elements of capping member 67 that are adapted for coupling with the protruding portions of piercing elements 30E can take various forms. For example, the protruding portions of piercing elements 30E can include hooked or barbed features adapted for entrapment in various corresponding openings or channels in capping member 67. In some embodiments, a circumferential channel can be employed to reduce locational constraints between the protruding portions of piercing elements 30E and capping member 67. It is understood that other forms of couplings can be employed in other example embodiments. In this example embodiment, capping member 67 is slid over elongated member 20E to locate it in proximity to the protruding portions of piercing elements 30E.

Figure 7:
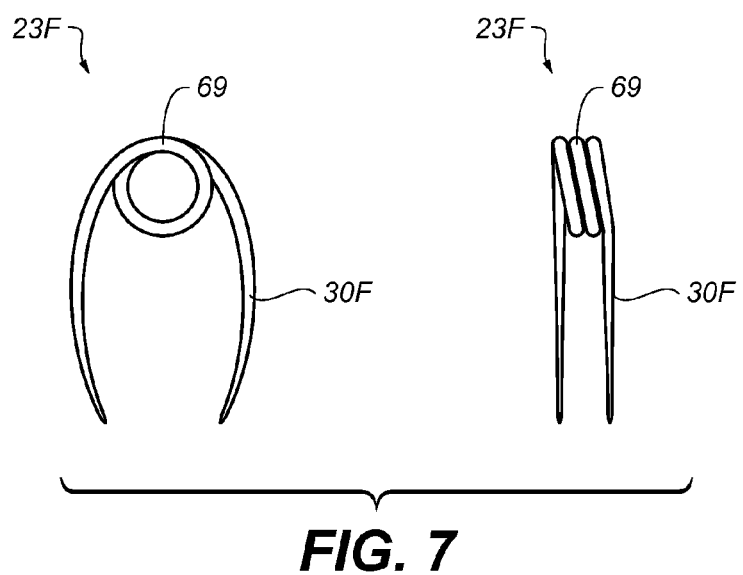
FIG. 7 includes front and side views of a clip employed in another example embodiment.

FIG. 7 includes front and side views of a clip 23F employed in another example embodiment. Clip 23F includes a plurality of piercing elements 30F that are coupled together by a bias member 69 (e.g. a torsional spring) that acts to enhance the elastic restorative force of the clip 23F.

Figure 8A:
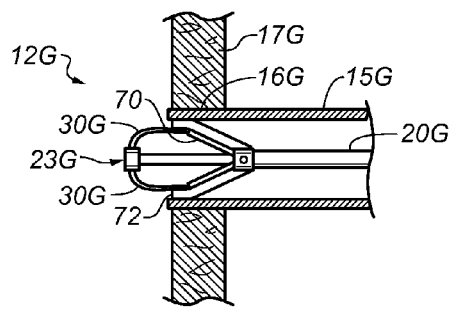
FIGS. 8A, 8B, 8C, 8D and 8E are schematic representations of various stages of a closing of a first opening in an anatomical cavity as per another example embodiment.
Figure 8D:
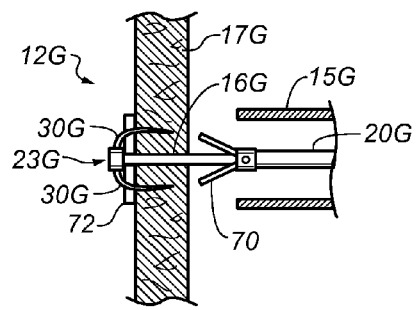
Figure 8B:
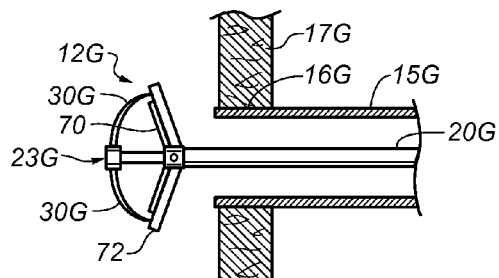

FIGS. 8A, 8B, 8C, 8D and 8E include schematic representations of various stages of a closing of a first opening 16G in an anatomical cavity 12G as per another example embodiment. As shown in FIG. 8A, tubular member 15G is utilized to deliver a clip 23G through first opening 16G that is provided in a tissue wall 17G that surrounds a portion of anatomical cavity 12G. In this example embodiment, clip 23G is releasably coupled to an elongated member 20G arranged to advance clip 23G through tubular member 15G. In this example embodiment, deployment arms 70 capture the piercing elements 30G of clip 23G in a manner similar to that taught in commonly assigned U.S. patent application Ser. No. 11/436,585. As best shown in FIG. 8B, a pad 72 is coupled to deployment arms 70 in a manner that causes pad 72 to extend beyond the ends of piercing elements 30G that are captured by the ends of deployment arms 70. In this example embodiment, pad 72 is elastic in nature and is stretched from an initial state to a configuration suitable for coupling with deployment arms 70. Without limitation, pad 72 can be coupled to deployment arms 70 by various methods including the use of adhesives or mechanical fastening systems. Pad 72 can be coupled to deployment arms 70 with a fastening system that breaks apart under the application of a predetermined force. As shown in FIG. 8A, deployment arms 70 can also position pad 72 in a retracted position suitable for passage through tubular member 15G. In some example embodiments, pad 72 includes an absorbent material. In some example embodiments, pad 72 is coupled to clip 23G.

Deployment arms 70 have been operated to outwardly extend the piercing elements 30E thereby imparting spring or potential energy into piercing elements 30G in FIG. 8B. Pad 72 is also shown in an extended position that also results from this operation of deployment arms 70. As shown in FIG. 8C, elongated member 20G is employed to exert a force on clip 23G to bring piercing elements 30G through pad 72 and into tissue wall 17G. During this procedure, deployment arms 70 are retracted while pad 72 is fixed in a larger stretched size due to the fixation by clip 23G into tissue wall 17G. At this point, it is possible to retract deployment arms 70 to a position within the confines of tubular member 15G, while pad 70 remains secured to tissue wall 17G by piercing elements 30G. In this example embodiment, pad 72 is an intermediate member positioned between clip 23G and tissue wall 17G.

FIG. 8D shows the constricted first opening 16G after tubing member 15G has been retracted from first opening 16G. Due to the retraction of tubing member 15G, first opening 16G has been constricted due to the elastic restorative forces of clip 23G. The elastic nature of pad 17 has caused the perimeter of pad 72 to decrease proportionately with the inward movement of piercing elements 30G. Deployment arms 70 have been retracted into the tubular member 15G and a portion of elongated member 20G remains coupled with clip 23G. This coupling allows clip 23G to be disengaged from the tissue wall 17G and redeployed if the closure of first opening 16G is deemed unsatisfactory.

Figure 8E:
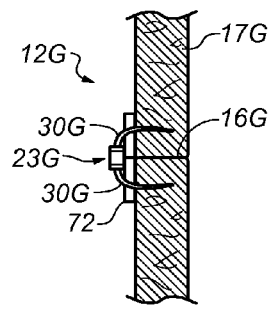
Figure 8C:
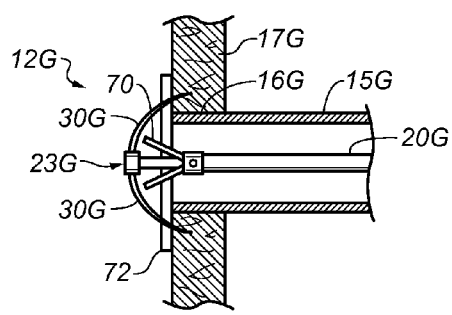

FIG. 8E shows the completely retracted elongated member 20G after the closure has been verified for haemostasis. In this case, elongated member 20G is decoupled from clip 23G, and is pulled through the first opening 16G. At this point, the complete assembly of tubular member 15G, elongated member 20G and deployment arms 70 can be removed from the patient.

Various example embodiments have been described in conjunction with closing a first opening 16 (e.g., first openings 16, 16A, 16B, etc.) through which a closure device 10 (e.g., closure devices 10, 10A, 10B, etc.) is passed into an anatomical cavity 12 (e.g., anatomical cavities 12, 12A, 12B, etc.). In some example embodiments, a first opening 16 is a naturally occurring opening. In some example embodiments, a first opening 16 is formed by factors such as disease. In some example embodiments, a first opening 16 is formed by factors such as trauma. In other example embodiments, a first opening 16 is formed with the use of a perforating member or instrument.

Figure 9:
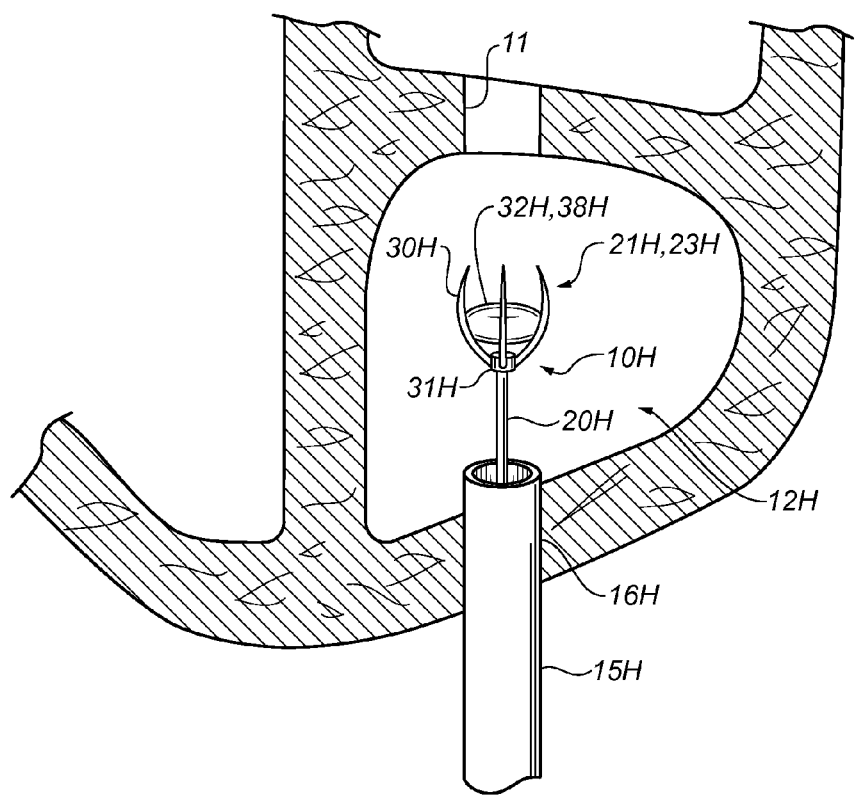
FIG. 9 is schematic view of a closure device according to an example embodiment that is employed to close an opening in an anatomical cavity that includes a plurality of openings.

In some example embodiments, one or more openings are closed, each of the one or more openings leading to an anatomical cavity 12. Each of the one or more openings that is closed can be natural opening, a man-made opening or an opening formed by other factors. For example, FIG. 9 is a schematic representation of an anatomical cavity 12H that include a plurality of openings including a first opening 16H and second opening 11. In this example embodiment, a closure device 10H is employed to close second opening 11. Closure device 10H is inserted into anatomical cavity 12H via a tubular member 15H inserted into a first opening 16H. In this example embodiment, closure device 10H includes a closure unit 21H that is operable to constrict a portion of second opening 11. In this example embodiment, closure unit 21H includes a clip 23H and an inflatable member 32H that are operated to constrict a portion of the second opening 11 in a manner similar to other example embodiments described in the present specification. In this example embodiment, clip 23B includes a plurality of piercing elements 30H coupled together by a hub 31H. Hub 31H is releasably coupled to elongated member 20H which is arranged to advance closure unit 21H through first opening 16H into anatomical cavity 12H.

Unlike other previously described example embodiments, the piercing elements 30H extend away from elongated member 20H in this example embodiment. This allows piercing elements 30H to be positioned for deployment into a surface of anatomical cavity 12H that includes second opening 11. Inflatable member 32H includes a flexible membrane 38H that is selectively moveable between a retracted position and an extended position. In a manner similar to other example embodiments, inflatable member 32H is employed to space piercing elements 30H apart when clip 23B is positioned within anatomical cavity 12H. Elongated member 20H and inflatable member 32H are further operated to deploy clip 23H into tissue surrounding second opening 11 to constrict a portion of second opening 11. The use of angiograms or other visual techniques can be employed to confirm that second opening 11 has been closed and haemostasis has been achieved. Once elongated member 20H has been decoupled from clip 23H, first opening 16H can also be closed by employing techniques various embodiments for closing a first opening 16 provided in this disclosure. Alternatively, other techniques may be employed to close first opening 16H if so desired. In some example embodiments, closure device 10H can include an orientation control unit 60 adapted for defining an orientation of a surface of anatomical cavity 12H that includes second opening 11. In some example embodiments, closure device 10H can include an intermediate member 35 positioned between clip 23H and a surface of anatomical cavity 12H that includes second opening 11, the intermediate member 35 arranged to be pierced by a piercing element 30H of clip 23H.

Without limitation, the various described embodiments can be combined to provide other example embodiments. All of any U.S. patent application publications, U.S. patent applications, foreign patent applications and non-patent publications referred to in this specification and/or listed in the Application Data Sheet including U.S. provisional application Ser. No. 61/352,277, filed Jun. 7, 2010, are incorporated herein by reference, in their entirety. Aspects of the various embodiments can be modified, if necessary, to employ systems, circuits and concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all medical treatment devices in accordance with the claims. Accordingly, the invention is not limited by the disclosure, but instead its scope is to be determined entirely by the following claims.

The invention claimed is:

1. A medical system configured to close one or more openings, each of the one or more openings leading to an anatomical cavity, at least a portion of the medical system sized in at least one configuration to be deliverable through a first opening of the one or more openings into the anatomical cavity, and the at least the portion of the medical system comprising:
   an elongated member, a portion of the elongated member sized to be deliverable through the first opening into the anatomical cavity;
   a closure unit releasably coupled to the elongated member and arranged to be delivered into the anatomical cavity to a location at least proximate an interior tissue surface within the anatomical cavity, the closure unit further arranged to close an opening of the one or more openings located on the interior tissue surface within the anatomical cavity; and
   an intermediate member releasably coupled to the elongated member and arranged to be delivered into the anatomical cavity to a location between at least part of the closure unit and the interior tissue surface within the anatomical cavity,
   wherein the closure unit comprises a plurality of piercing elements, each piercing element of the plurality of piercing elements arranged to point back toward the elongated member in a state where the closure unit is coupled to the elongated member, and each piercing element of the plurality of piercing elements arranged to pierce through the intermediate member and pierce through the interior tissue surface into tissue surrounding the anatomical cavity,
   wherein the at least the portion of the medical system further comprises a plurality of deployment arms that respectively capture the plurality of piercing elements in at least a first configuration of the medical system,
   wherein the intermediate member is coupled to the plurality of deployment arms in at least the first configuration of the medical system, and
   wherein the plurality of deployment arms position the intermediate member in a retracted position within a tubular member in at least a second configuration of the medical system, at least a portion of the tubular member sized to be deliverable into the first opening.

2. The medical system of claim 1 wherein the closure unit is arranged to close the opening located on the interior tissue surface within the anatomical cavity by piercing through the interior tissue surface into the tissue surrounding the anatomical cavity to constrict a portion of the opening of the one or more openings located on the interior tissue surface within the anatomical cavity.

3. The medical system of claim 1 wherein the plurality of deployment arms respectively releasably capture respective tissue-piercing tips of the plurality of piercing elements.

4. The medical system of claim 1 wherein respective ends of the plurality of deployment arms respectively capture the plurality of piercing elements in at least the first configuration of the medical system.

5. The medical system of claim 1 wherein the intermediate member extends beyond ends of the plurality of piercing elements in at least the first configuration of the medical system.

6. The medical system of claim 1 wherein the intermediate member is elastic.

7. The medical system of claim 1 wherein the intermediate member is elastic and is stretched from an initial state when coupled to the plurality of deployment arms in at least the first configuration of the medical system.

8. The medical system of claim 1 wherein the intermediate member includes an absorbent material.

9. The medical system of claim 1 wherein the plurality of deployment arms are decoupled from the plurality of piercing elements in at least a third configuration of the medical system.

10. The medical system of claim 9 wherein each of the plurality of piercing elements is arranged to pierce through the intermediate member into the interior tissue surface within the anatomical cavity in at least the second configuration of the medical system.

11. The medical system of claim 1 wherein the plurality of deployment arms outwardly extend the plurality of piercing elements in at least the first configuration of the medical system as compared to the second configuration of the medical system where the plurality of deployment arms retain the plurality of piercing elements in a retracted position sized to be deliverable through the tubular member.

12. The medical system of claim 1 wherein the intermediate member is a pad.

13. The medical system of claim 1 wherein at least a portion of the intermediate member is parallel to at least a portion of at least one of the plurality of deployment arms in at least the first configuration.

14. The medical system of claim 1 wherein the closure unit comprises a clip, and wherein the elongated member is configured to exert a force on the clip to bring the at least one piercing element through the intermediate member into the interior tissue surface.

15. The medical system of claim 1 wherein the closure unit comprises a clip, and wherein the clip is configured to cause the at least one piercing element to constrict the first opening via an elastic restorative force of the clip in at least one configuration of the medical system.

16. A method of operating a medical system for closing one or more openings, each of the one or more openings leading to an anatomical cavity, the medical system sized in at least one configuration to pass through a lumen of a tubular member and a first opening of the one or more openings into the anatomical cavity, the method comprising:
   outwardly extending a plurality of piercing elements of a closure unit of the medical system to cause at least tissue-piercing tips of the plurality of piercing elements to outwardly extend beyond a perimeter of the lumen of the tubular member from a retracted position in which at least the plurality of piercing elements is arranged to be deliverable through the lumen of the tubular member, the closure unit arranged to be delivered into the anatomical cavity to a location at least proximate an interior tissue surface within the anatomical cavity, and the closure unit further arranged to close an opening of the one or more openings located on the interior tissue surface within the anatomical cavity; and causing the tissue-piercing tips of the outwardly-extended plurality of piercing elements to pierce, via a pulling motion of the closure unit toward the tubular member, through an intermediate member of the medical system, the intermediate member arranged at a position between at least a non-piercing portion of the plurality of piercing elements and the tubular member when the plurality of piercing elements are outwardly extended beyond the retracted position, the tissue-piercing tips of the outwardly-extended plurality of piercing elements configured to pierce, via the pulling motion of the closure unit toward the tubular member, through the intermediate member into the interior tissue surface within the anatomical cavity.

17. The method of claim 16 wherein the outwardly extending of the plurality of piercing elements results in placing the intermediate member in an extended position in which the intermediate member extends outwardly from the tubular member.

18. The method of claim 16 wherein the causing is effected by employing an elongated member of the medical system to exert a pulling force on the closure unit to bring the tissue-piercing tips of the plurality of piercing elements through the intermediate member, a portion of the elongated member sized to be deliverable through the lumen of the tubular member, and wherein each of the closure unit and the intermediate member is coupled to the elongated member with the plurality of piercing elements pierced through the intermediate member.

19. The method of claim 18, further comprising, after the causing, de-coupling the elongated member from each of the closure unit and the intermediate member and retracting the elongated member.

* * * * *